(12) United States Patent
Hosokawa

(10) Patent No.: US 9,039,972 B2
(45) Date of Patent: May 26, 2015

(54) APPARATUS FOR MONITORING THROMBUS FORMATION

(71) Applicant: FUJIMORI KOGYO CO., LTD., Tokyo (JP)

(72) Inventor: Kazuya Hosokawa, Tokyo (JP)

(73) Assignee: FUJIMORI KOGYO CO., LTD., Tokyo (JP)

( * ) Notice: Subject to any disclaimer, the term of this patent is extended or adjusted under 35 U.S.C. 154(b) by 52 days.

(21) Appl. No.: 13/716,221

(22) Filed: Dec. 17, 2012

(65) Prior Publication Data

US 2013/0164176 A1 Jun. 27, 2013

Related U.S. Application Data

(62) Division of application No. 12/083,787, filed as application No. PCT/JP2006/320789 on Oct. 18, 2006, now Pat. No. 8,372,342.

(30) Foreign Application Priority Data

| Oct. 18, 2005 | (JP) | 2005-302557 |
| Oct. 24, 2005 | (JP) | 2005-308065 |
| Nov. 18, 2005 | (JP) | 2005-334594 |
| Dec. 13, 2005 | (JP) | 2005-358448 |
| Feb. 14, 2006 | (JP) | 2006-036148 |
| Aug. 30, 2006 | (JP) | 2006-234270 |

(51) Int. Cl.
G01N 33/86 (2006.01)
(52) U.S. Cl.
CPC .................................. *G01N 33/86* (2013.01)
(58) Field of Classification Search
CPC .................................................... G01N 33/86
USPC .................. 422/68.1, 400, 402, 82.05, 82.08
See application file for complete search history.

(56) References Cited

U.S. PATENT DOCUMENTS

| 5,662,107 A | 9/1997 | Sakariassen |
| 2002/0071788 A1 | 6/2002 | Fujii et al. |

(Continued)

FOREIGN PATENT DOCUMENTS

| CN | 1138377 | 12/1996 |
| EP | 1443325 | 8/2004 |

(Continued)

OTHER PUBLICATIONS

Orvim et al., "Effect of Selective Factor Xa Inhibition on Arterial Thrombus Formation Triggered by Tissue Factor/Factor VIIa or Collagen in an Ex Vivo Model of Shear-Dependent Human Thrombogenesis", Arteriosclerosis, Thrombosis, and Vascular Biology, 1995, pp. 1-23.

(Continued)

*Primary Examiner* — Sam P Siefke
(74) *Attorney, Agent, or Firm* — Jianq Chyun IP Office

(57) ABSTRACT

An apparatus for monitoring thrombus formation wherein anticoagulated blood is flown through a channel simulating a blood vessel while releasing the anticoagulant treatment or promoting blood coagulation to thereby monitor thrombus formation. This apparatus for monitoring thrombus formation comprises: a thrombus formation chamber in at least a part of which a thrombus formation inducer inducing thrombus formation is provided; an inlet tube which is connected to the thrombus formation chamber and through which blood is flown into the thrombus formation chamber; and a drug tube which is connected to the inlet tube and through which a drug releasing the anticoagulant treatment or a drug promoting blood coagulation is supplied.

8 Claims, 9 Drawing Sheets

(56) References Cited

U.S. PATENT DOCUMENTS

2004/0143174 A1 7/2004 Brubaker
2006/0160165 A1* 7/2006 Phillips et al. .................. 435/13

FOREIGN PATENT DOCUMENTS

| JP | 04-152952 | 5/1992 |
|---|---|---|
| JP | 05-260950 | 10/1993 |
| JP | 07-136197 | 5/1995 |
| JP | 2004-522146 | 7/2004 |
| JP | 2004-251630 | 9/2004 |
| JP | 2006-145345 | 6/2006 |
| WO | 9600899 | 1/1996 |
| WO | 0004388 | 1/2000 |
| WO | 0043794 | 7/2000 |
| WO | 0250534 | 6/2002 |
| WO | 2004024026 | 3/2004 |
| WO | 2004068138 | 8/2004 |

OTHER PUBLICATIONS

Eric F. Grabowski, Platelet Aggregation in Flowing Blood at a Site of Injury to an Endothelial Cell Monolayer; Quantitation and Real-Time Imaging with the TAB Monoclonal Antibody, The American Society of Hematology, Jan. 15, 1990, pp. 390-398, vol. 75, No. 2.

Tsuji et al., "Real-Time Analysis of Mural Thrombus Formation in Various Platelet Aggregation Disorders: Distinct Shear-Dependent Roles of Platelet Receptors and Adhesive Proteins Under Flow", The American Society of Hematology, Aug. 1, 1999, pp. 968-975, vol. 94, No. 3.

* cited by examiner (A)

(B)

(C)

(A)

(B)

(A)

(B)

(C)

APPARATUS FOR MONITORING THROMBUS FORMATION

CROSS-REFERENCE TO RELATED APPLICATION

This application is a divisional of and claims the priority benefit of U.S. application Ser. No. 12/083,787, filed on Aug. 28, 2009, now allowed, which is a 371 of international application of PCT application serial no. PCT/JP2006/320789, filed on Oct. 18, 2006, which claims the priority benefit of Japan application no. 2005-302557, filed on Oct. 18, 2005, Japan application no. 2005-308065, filed on Oct. 24, 2005, Japan application no. 2005-334594, filed on Nov. 18, 2005, Japan application no. 2005-358448, filed on Dec. 13, 2005, Japan application no. 2006-036148, filed on Feb. 14, 2006 and Japan application no. 2006-234270, filed on Aug. 30, 2006. The entirety of each of the above-mentioned patent applications is hereby incorporated by reference herein and made a part of this specification.

TECHNICAL FIELD

The present invention relates to a method of monitoring efficacy of an antithrombotic drug administered to a patient or the like, and specifically, to an apparatus for and a method of comprehensively evaluating blood coagulation and platelet thrombus formation under a bloodstream-equivalent environment with a whole blood or plasma containing platelets.

BACKGROUND ART

For example, the atherothrombosis such as the myocardial infarction causes serious thrombus formation such that an atheromatous plaque is broken at an arteriosclerosis site, platelets are adhered on collagen including tissue factor exposed to the bloodstream. Further, the platelet aggregation, the activation of a blood coagulation system, and the like complexly occur resulting in serious obstructive thrombus. Heart disease such as myocardial infarction, is a serious disease and is the second leading cause of overall deaths in Japan.

However, thrombus formation proceeds only in an atherosclerotic region in the myocardial infarction, and a thrombotic tendency in the whole body is not extremely proceeded. In-vitro examinations are unsuitable for evaluating the thrombotic tendency in such a thrombosis and the monitoring of the antithrombotic effect in the antithrombotic therapy. Thus, it is important to make comprehensive evaluations on coagulation and platelets (adhesion and agglutination) in the presence of the bloodstream.

Heretofore, the blood coagulability has been evaluated by determining activated partial thromboplastin time (APTT), thromboplastin time (PT) using the plasma. The APTT mainly reflects intrinsic coagulation and the PT mainly reflects extrinsic coagulation. The examination of blood platelets is carried out by using platelet-rich plasma and adding a platelet-activating substance such as ADP or collagen to thereby evaluate the aggregating property of platelets from a change in transmittance thereof or the like. In addition, the coagulation time of the whole blood can be determined with the whole blood clotting time, the whole blood clotting time after calcium re-addition, and the like.

Further, an examination system using the whole blood employs thromboelastogrm, which monitors the activations of clotting factors, the platelet agglutination, and the like.

However, thrombus grows under a blood flow in vivo. In contrast, the above examination method or the like is determined in-vitro that is in the closed state. Thus, the status of in-vivo thrombus growth cannot be observed.

As proposals for solving the above problems, Patent Document 1 and Non-patent Documents 2 and 3 disclose the method including bringing the blood provided with an antithrombotic drug to be evaluated to pass on a collagen cell and monitoring the adhesion or agglutination of the platelets by fluorescently-labeling the platelets with a confocal microscope.

However, in the invention described in the document the observation is carried out under the presence of an anticoagulation drug. Thus, the fact that a thrombus which is caused by the adhesion or agglutination of platelets induced by the blood coagulation system is not formed or decreased property to form thrombus is evaluated by monitoring a morphological change in platelet. Thus, the evaluation does not reflect the platelet activation interlocking with coagulation system. Therefore, such an invention is favorable for the evaluation of the efficacy of an antiplatelet drug but is unable to monitor a thrombus itself and the whole process of thrombus formation. In addition, a fluorescence microscope is expensive, so it can be hardly used for general examination.

Further, in Patent Document 2, the fluidity of the anticoagulated blood is determined by passing the blood through a fine-comb-like silicon cell. Likewise, the process of Patent Document 2 also uses the anticoagulated blood, so the influence of a coagulation system cannot be determined. In addition, the viscosity of blood in the process has large individual variations and in diurnal variations, so it is difficult to reflect drug therapy using the system.

The platelet is activated by the coagulation system, and the coagulation system is promoted by activated platelets. Therefore, the efficacy of an antithrombotic drug cannot be observed in the anticoagulated blood, because activation of platelet is also suppressed by the anticoagulation treatment. In addition, non-anticoagulated blood can not used in an examination, because it promptly forms is clot.

Patent Document 1: JP 2004-251630 A
Patent Document 2: JP 2006-145345 A
Non-patent Document 1: Blood. 1990; 75:390-398
Non-patent Document 2: Blood. 1999; Aug. 1: 94(3):968-75

DISCLOSURE OF THE INVENTION

The present invention has been made in consideration of the above circumstances and intends to provide an apparatus and method of comprehensively evaluating the thrombus formation due to the blood coagulation and platelet under a bloodstream-equivalent environment with a whole blood or plasma containing platelets (in the specification of the present invention, they may be inclusively referred to as "blood"), when monitoring the efficacy of an antithrombotic drug administered to a patient or the like.

Means for Solving the Problems

To solve the above-mentioned problems, the present invention provides an apparatus for monitoring thrombus formation, which monitors thrombus formation by flowing anticoagulated blood through a channel that simulates a blood vessel while releasing an anticoagulation treatment or promoting a blood coagulation, comprising: a thrombus formation chamber in at least a part of which a thrombus inducing material that induces thrombus formation is provided; an inlet tube which is connected to the thrombus formation chamber and through which blood is flown into the thrombus formation chamber; and a drug tube which is connected to the inlet tube and through which a drug that promotes blood coagulation (hereinafter may be referred to as "coagulation promotion") or a drug that releases the anticoagulation treatment is supplied. In the present invention, the term "monitoring" means not only visual evaluation of thrombus formation with eyes, an imaging, but also evaluation of the degree of thrombus formation in numerical terms by pressure determination or the like.

Further, the present invention provides an apparatus for monitoring thrombus formation which comprises a thrombus formation chamber in at least a part of which a thrombus inducing material that induces thrombus formation is provided; an inlet tube which is connected to the thrombus formation chamber and through which blood is flown into the thrombus formation chamber; and a thrombus formation inhibitor inlet tube which is connected to the thrombus formation chamber and mixes a thrombus formation inhibitor with the blood after passing through the thrombus formation chamber.

In this case, the apparatus for monitoring thrombus formation is preferably formed on a substrate.

The apparatus for monitoring thrombus formation of the present invention preferably further comprises a pump for pressurizing the inlet tube and/or the drug tube or a pump for aspirating a discharge tube which is connected to the thrombus formation chamber and provided for discharging the blood from the thrombus formation chamber.

The apparatus for monitoring thrombus formation of the present invention preferably further include a pressure-measuring apparatus and a camera for taking images of a thrombus formation chamber.

Further, the thrombus inducing material preferably comprises collagen.

More preferably, the thrombus inducing material further comprises a tissue factor (tissue thromboplastin).

Further, the present invention provides a method of monitoring thrombus formation, comprising: flowing anticoagulated blood into a thrombus formation chamber, in at least a part of which a thrombus inducing material inducing thrombus formation is provided, while releasing an anticoagulation treatment or promoting a blood coagulation to thereby monitor thrombus formation. In the present invention, the term "flowing the blood while releasing the anticoagulation treatment or promoting blood coagulation" may be a state where an anticoagulation-releasing reaction or a coagulation-promoting reaction in the channel is being occurred, and includes a state where an drug that releases an anticoagulation releasing agent, or a coagulation promoting agent is flown while mixing with the blood in the channel or a state where the anticoagulation releasing agent or the coagulation promoting agent is promptly flown after mixing with the blood.

In the method of monitoring thrombus formation of the present invention, it is preferable that the anticoagulation treatment is a treatment with a calcium chelator such as citric acid and the anticoagulation treatment is released with a free calcium donor.

In the method of monitoring the thrombus formation of the present invention, it is preferable that the anticoagulation treatment is a treatment with a thrombin aptamer and the anticoagulation treatment is released with the antisense DNA of the thrombin aptamer.

Here, in the method of monitoring thrombus formation of the present invention, it is preferable to monitor the thrombus formation by flowing anticoagulated blood into a thrombus formation chamber, while promoting blood coagulation without releasing the anticoagulation treatment. In this case, a means for promoting the blood coagulation is preferably the addition of tissue thromboplastin.

In addition, in the method of monitoring thrombus formation of the present invention, the blood which has been anticoagulated with one kind or more kinds of anticoagulation agents is preferably released form the anticoagulation treatment with at least one kind of anticoagulation treatment releasing agent that corresponds to the anticoagulation treatment agent used. Here, it is preferable that the anticoagulation treatment agents are a contact phase factor inhibitor and a calcium chelator, and the anticoagulation treatment releasing agent is a free calcium donor. Further, it is also preferable that the anticoagulation treatment agents are a contact phase factor inhibitor and heparin, and the anticoagulation treatment releasing agent is heparinase. Further, it is also preferable that the anticoagulation treatment agents are an inhibitor for a contact phase factor such as a blood coagulation XII factor, kallikrein, or the like and a thrombin aptamer, and the anticoagulation treatment releasing agent is the antisense DNA of the thrombin aptamer. The inhibitor for the blood coagulation XII factor is preferably a maize-derived trypsin inhibitor.

In the method of monitoring thrombus formation of the present invention, it is preferable to determine the pressure at the time of inflow and/or outflow of the blood in the thrombus formation chamber.

In the method of monitoring thrombus formation of the present invention, the thrombus inducing material preferably comprises collagen and a tissue factor.

Effects of the Invention

According to an apparatus for monitoring thrombus formation of the present invention, the apparatus comprises: a thrombus formation chamber in at least a part of which a thrombus inducing material that induces thrombus formation is provided; an inlet tube which is connected to the thrombus formation chamber and through which blood is flown into the thrombus formation chamber; and a drug tube which is connected to the inlet tube and through which a drug that releases the anticoagulation treatment or a drug that promotes blood coagulation is supplied. Therefore, the anticoagulated blood, which is treated in order to prevent the blood collected after administering the antithrombotic drug to a patient from coagulating in the channel extending to the thrombus formation chamber, can be monitored by intentionally forming a thrombus in a thrombus formation chamber. Thus, the efficacy of an antithrombotic drug can be specifically monitored in the environment similar to the inside of the human body. In addition, an anticoagulation treatment agent can be used at the time of blood sampling. Therefore, there is an advantage in that samples after the blood sampling can be stored for a certain period of time and the examination time can be randomly selected.

According to another apparatus for monitoring thrombus formation of the present invention, the apparatus comprises: a thrombus formation chamber in at least a part of which a thrombus inducing material that induces thrombus formation is provided; an inlet tube which is connected to the thrombus formation chamber and through which blood is flown into the thrombus formation chamber; and an inlet for a thrombus formation inhibitor, which is connected to the thrombus formation chamber and mixes the thrombus formation inhibitor with the blood after passing through the thrombus formation chamber. Therefore, the thrombus observation can be carried out in a manner as described above. In addition, the blood coagulation does not proceed downstream in the thrombus formation chamber, therefore, influence on the pressure determination can be prevented and more delicate pressure changes can be monitored.

A small amount of blood can be monitored when the apparatus for monitoring thrombus formation of the present invention is formed on a substrate. In addition, the apparatus is provided with a pump for pressurizing the inlet tube and/or the drug tube or a pump for aspirating a discharge tube which is connected to the thrombus formation chamber and provided for discharging the blood from the thrombus formation chamber. Therefore, the blood and the drug for promoting blood coagulation can be stably flown for a predetermined period of time at predetermined pressure or predetermined flow rate.

If the apparatus for monitoring thrombus formation of the present invention comprises a pressure-measuring apparatus, the degree of thrombus formation can be converted into numbers, so a quantitative evaluation can be performed.

The apparatus can be easily set when the thrombus inducing material comprises collagen. Thrombus formation can be efficiently induced when the thrombus inducing material further comprises a tissue factor such as tissue thromboplastin together with collagen.

Further, if the apparatus for monitoring thrombus formation of the present invention comprises a camera for taking an image of the thrombus formation chamber, the appearance of the thrombus formation can be observed as an image and the image can be then stored.

Further, according to a method of monitoring thrombus formation of the present invention, the method comprises: monitoring thrombus formation by flowing anticoagulated blood through a thrombus formation chamber in at least a part of which a thrombus inducing material that induces thrombus formation is provided, while releasing the anticoagulation treatment or promoting blood coagulation. Thus, the thrombus formation on the thrombus inducing material can be monitored by flowing the anticoagulated blood, which is obtained by anticoagulating the blood collected after administering the antithrombotic drug to a patient to prevent coagulation, while promoting blood coagulation. Therefore, the efficacy of an antithrombotic drug can be specifically monitored in the environment similar to the inside of the human body. In addition, an anticoagulation agent can be used for blood sampling. Therefore, there is an advantage in that samples after the blood sampling can be stored for a certain period of time and the examination time can be randomly selected. If the anticoagulation treatment is a treatment with a calcium chelator such as citric acid and the anticoagulation treatment is released by a free calcium donor, the reagent can be easily obtained and thus it is preferable. If the anticoagulation treatment is a treatment with a thrombin aptamer and the anticoagulation treatment is released by the antisense DNA of the thrombin aptamer, it is possible to carry out the examination while reflecting the physiological calcium ion concentration of the blood.

In addition, according to another method of monitoring thrombus formation of the present invention, it is able to monitor thrombus formation by flowing anticoagulated blood into the thrombus formation chamber without performing the operation of releasing the anticoagulation treatment, while prompting blood coagulation. Therefore, the thrombus formation can be observed with a small amount of the blood and the burden of the subject can be reduced. In this case, further, the drug tube is not always required, so the apparatus for monitoring thrombus formation can be simplified. Here, if tissue thromboplastin is used as a blood coagulation promoting agent, the blood coagulation can be promoted by activating the coagulation system in an alternative pathway that avoids the XII-factor activation and the kallikrein activation to thereby monitor thrombus formation in the thrombus formation chamber.

Further, the thrombus formation can be monitored with a simple operation by releasing the anticoagulated blood obtained using one kind or more kinds of anticoagulation treatment agents with at least one kind of anticoagulation treatment releasing agent corresponding to the anticoagulation treatment agent used. In this case, when an anticoagulation treatment is carried out with a contact phase factor inhibitor and a calcium chelator, and the anticoagulation treatment is released with a free calcium donor, or when an anticoagulation treatment is carried out with a contact phase factor inhibitor, and heparin and the anticoagulation treatment is released with heparinase, the anticoagulation treatment exerting an effect at the time of monitoring thrombus formation is an anticoagulation treatment with the contact phase factor inhibitor, therefore monitoring of thrombus formation can be performed under more physiological conditions, particularly while reflecting a divalent metal ion associated with thrombosis, such as calcium or magnesium. In this case, when the anticoagulation treatment is carried out with an inhibitor of a contact phase such as a blood coagulation XII factor or kallikrein and a thrombin aptamer, and then the anticoagulation treatment is released by the antisense DNA of the thrombin inhibition aptamer, the blood can be stored over a prolonged period. Further, the anticoagulation treatment can be efficiently carried out when a maize-derived trypsin inhibitor is used as the inhibitor of the blood coagulation XII factor.

If the method of monitoring thrombus formation of the present invention performs the measurement of pressure at the time of inflow and/or outflow of the blood in the thrombus formation chamber, the degree of thrombus formation can be converted into numbers, so a quantitative evaluation can be easily performed by an extremely simple apparatus.

Further, if the thrombus inducing material comprises collagen and the tissue factor, the apparatus can be easily set and the thrombus formation can be effectively induced.

DESCRIPTION OF REFERENCE NUMERALS

1 . . . apparatus for monitoring thrombus formation,
10, 110, 311, 411 . . . thrombus formation chamber,
11, 111 . . . inlet tube,
12, 112, 312 . . . drug tube,
13, 313, 413 . . . discharge tube,
14, 114 . . . constriction portion,
15, 115, 315 . . . thrombus inducing material,
16 . . . generated thrombus,
20, 21, 320, 420 . . . syringe,
30, 31, 330, 331, 414, 423 . . . pump,
40, 41, 340 . . . pressure sensor,
100 . . . substrate (main body of microchip),
200 . . . substrate (cover of microchip),
100A, 100B, 100C . . . connection part,
100D . . . circuit to be pressure gauge,
100E . . . regulation valve,
300, 400 . . . microchip (apparatus for monitoring thrombus formation),
306 . . . pump control unit,
307 . . . computer,
308 . . . fluorescent stereoscopic microscope with CCD camera,
317 . . . pressure inlet tube,
322, 422 . . . blood caoagulation inhibitor inlet,
412 . . . connection tube,
430 . . . CCD camera,
431 . . . lens,
432 . . . illumination optical source,
433 . . . rail for moving camera,
A, B . . . thrombus-monitoring system

BEST MODE FOR CARRYING OUT THE INVENTION

Hereinafter, the present invention will be described with reference to the attached drawings in accordance the best mode.

Figure 1:
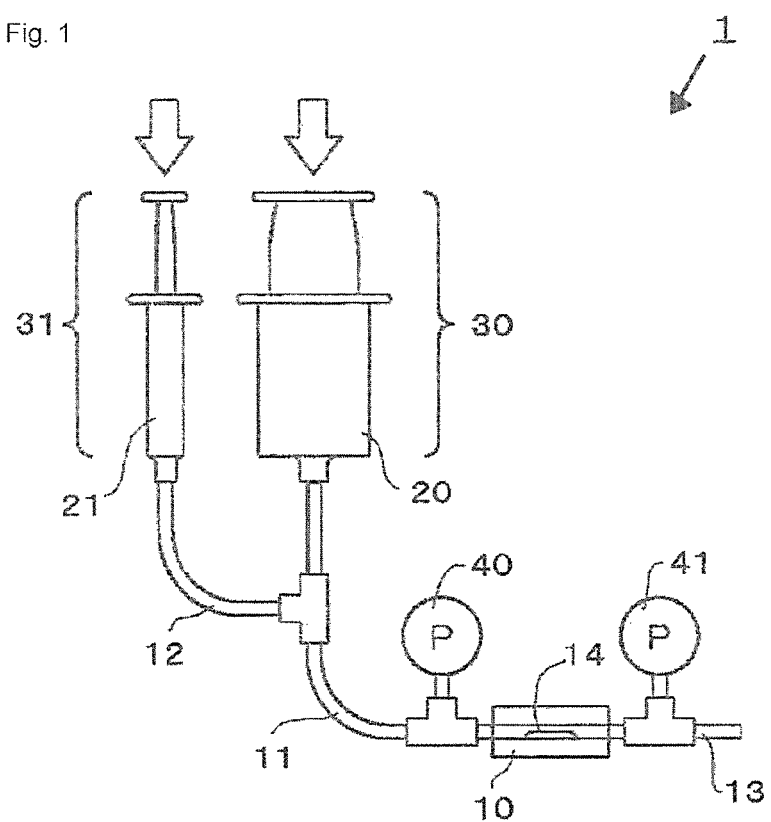
FIG. 1 is a schematic diagram illustrating an apparatus for monitoring thrombus formation according to a first embodiment of the present invention.

FIG. 1 is a schematic diagram illustrating a first embodiment of the apparatus for monitoring thrombus formation of the present invention.

As shown in FIG. 1, the apparatus 1 for monitoring thrombus formation of this embodiment comprises a thrombus formation chamber 10; an inlet tube 11 which is connected to the thrombus formation chamber and through which blood is flown into the thrombus formation chamber; and a drug tube 12 which is connected to the inlet tube and through which a drug that releases the anticoagulation treatment or a drug that promotes blood coagulation is supplied.

The thrombus formation chamber 10 is in the form of a substantially cylindrical shape provided with a thrombus-inducing material that induces thrombus formation in a part of the inside thereof and can be produced from a transparent glass, a thermoplastic resin, or the like. Examples of the thrombus inducing material include collagen, vWF (von Willebrand factor), previously-prepared thrombus, and fibrous substrates of silk, cotton, or the like. These materials may be used solely or in combination of two or more thereof. Among them, collagen is particularly preferable because it can be easily obtained, easily handled, and provided as a model similar to the actual blood vessel. The collagen may comprise a tissue factor. The thrombus inducing material of collagen or vWF is preferably in a state of being coated inside of the thrombus formation chamber 10 to prevent the thrombus inducing material from outflowing with the blood flow. Coating can be easily performed, for example, as described in JP 05-260950 A or Blood. 1995 Apr. 1; 85(7): 1826-35, by dissolving collagen in an acidic solution and dipping therein a substrate having hydrophillicity such as glass or polystyrene, followed by washing and drying to coat the surface of the material.

Further, it is preferable that the thrombus inducing material of a fibrous material or a previously-prepared thrombus may be in a state of being fixed in the inside of the thrombus formation chamber 10. Further, by impregnating a hygroscopic thin fibrous material such as cotton, nonwoven fabric, or fabric cloth with collagen, and drying them, a thrombus inducing material with a higher thrombus inducing ability can be obtained. In addition, substrate may be dipped in a collagen solution containing tissue thromboplastin and then dried to further enhance the thrombus-inducing ability thereof.

The thrombus inducing material can be selected depending on the inner diameter of the thrombus formation chamber 10 and the monitoring object. When atherothrombosis such as myocardial infarction is provided for a model, it is preferable to contain collagen solely or contain both collagen and tissue thromboplastin. In addition, it is more preferable that a constriction portion may be formed on the channel in the thrombus formation chamber to provide the thrombus formation chamber with a shearing stress. Further, in the case of a thrombus examination of cardiac cerebral infarction of cardiac origin or the like, in which a thrombus may be transferred from another portion with blood flow and adhered to occlude the blood vessel of another portion, it is preferable that a small amount of thrombus is previously adhered to the thrombus formation chamber 10 and provided as a thrombus inducing material, followed by monitoring the growth of thrombus formed thereon. In the case of a thrombosis examination of the blood capillary, the inside of the channel in the thrombus formation chamber may be divided into a plurality of channels each having a narrowed width or thickness of 10 to 30 μm. If the thrombus formation chamber 10 has a constriction portion with 100 μm or less in width or thickness, the channel may be occluded with a small amount of thrombus formed in such a constriction portion. Therefore, there is no need of using an additional thrombus inducing material, so the thrombus formation can be monitored by a blood coagulation promoting agent or an anticoagulation releasing agent. Therefore, the present invention includes this constriction portion as a thrombus inducing material.

The thrombus inducing material may be only coating with collagen or vWF. The thrombus formation chamber 10 at the coating portion may be preferably constricted and provided for a constriction portion 14, so high shearing stress-induced platelet aggregation can be monitored. In the case of coating with collagen as a thrombus inducing material, it is preferable that at least the substrate at a portion to be provided for a base is made of flat glass or plastic to obtain excellent adhesiveness. In addition, a portion on which the thrombus formation chamber 10 or a portion where the thrombus inducing material of the thrombus formation chamber 10 to be formed may be constructed as a detachable cassette. This case is preferable because the resulting thrombus can be easily washed or observed, or the thrombus inducing material can be easily exchanged with new one. In this case, the cassette may form a liquid-tight connection with a silicon rubber O-ring or the like. Preferably, the end of the cassette opposite to the end thereof connecting to the inlet tube 11 of the thrombus formation chamber 10 may be connected to a discharge tube 13 that permits discharge of the blood. Preferably, the discharge tube 13 may be divided with a cheese and the tip thereof may be then provided with a pressure gauge 41 such as a diaphragm-type one. On the other hand, the tip of the discharge tube 13 is preferably connected to a storage container (not shown).

The inlet tube 11 connected to the thrombus formation chamber 10 can be made using a transparent glass, a thermoplastic resin, or the like. The end of the inlet tube 11, which is opposite to the other end thereof connecting to the thrombus formation chamber 10, is connected to a syringe 20 that supplies blood. The syringe 20 is connected to a pump 30 and a pressing means (not shown) so that the plunger of the syringe 20 is pressed at predetermined pressure. The pump may be a general pump commercially available. Alternatively, the pump may be a syringe pump constructed by extruding the syringe with air at a constant pressure, or inverting the syringe so that the plunger is on the top side, and placing a weight on the plunger.

The inlet tube 11 may be preferably divided by a cheese and the end thereof is preferably provided with a pressure gauge 40 such as a diaphragm-type one at a part of the inlet tube 11 near the thrombus formation chamber 10.

The blood in the syringe 20 is subjected to an anticoagulation treatment. Examples of the anticoagulation treatment agent used in the anticoagulation treatment include sodium citrate or potassium citrate, sodium oxalate or potassium oxalate, Acid Citrate Dextrose (ACD), and ethylenediaminetetraacetate (EDTA). Such an anticoagulation treatment agent may be used in the form of powder, a lyophilized product, or a solution such as an aqueous solution. Among these anticoagulation agents, general 3.2% sodium citrate is preferable because it is easily obtainable. In this case, one volume of the anticoagulation treatment agent is preferably mixed with 9 volumes of blood.

In general, the whole blood or plasma without an anticoagulation treatment agent is coagulated within several minutes. The coagulation can be reduced or eliminated by the addition of a calcium chelator such as citrate. In particular, it has been reported that citrate can inhibit the agglutination and functions of prothrombinase and exogenous and intrinsic tenase.

The citrate-treated blood can be stored in liquid form for a predetermined period of time (for example, from several hours to several days) and processed into blood preparations such as a product of cytapheresis, platelet-rich plasma, and platelet-poor plasma. The citrate-containing plasma can be stored at about $-70°$ C. or lower for a prolonged period (from several months to several years). In the present invention, the whole blood and the plasma can be also used and, in this case, calcium or the like may be preferably added again.

However, in general, the whole blood or plasma added with calcium again is spontaneously coagulated due to contact activation in any of most storage containers. In this case, the contact activation may occur within about 2 to 4 minutes. On this account, in the present invention, the blood newly prepared by a citrate treatment after blood sampling, the blood prepared by a citrate treatment after being frozen for storage and then defrosted, or platelet-containing plasma may be added with an anticoagulation releasing agent such as calcium, just after monitoring thrombus.

Other anticoagulation agents may include heparin, hirudin, hirulog (peptide of hirudin C-terminal region), aprotinin, antithrombin antibody, thrombin aptamer, maize-derived trypsin inhibitor (1977, J. Biol. Chem 252, 8105). These materials inhibit blood coagulation by inhibiting a coagulation cascade as a result of inhibiting a blood coagulation factor, so they will be sometimes referred to as "coagulation-factor inhibitors" in the specification of the present invention.

The blood for monitoring can be sampled by any method such as a method in which coagulation-factor inhibitor is previously placed in a syringe or a vacuum blood-collecting vessel and the blood is then collected, or a method in which a coagulation-factor inhibitor is quickly added to the blood just after the blood sampling, to thereby obtain anticoagulated blood.

Further, the blood is collected in a vacuum blood-collecting vessel containing a coagulation-factor inhibitor such as heparin, and then heparinase and an anticoagulation treatment agent suitable for the monitoring object are added to degrade heparin so that hepatin is replaced by an anticoagulation treatment agent suitable for the monitoring object. In addition, the blood is collected in a vacuum blood-collecting vessel containing citric acid and then added with calcium chloride and a coagulation-factor inhibitor suitable for the monitoring object, such as a maize-derived trypsin inhibitor, or a thrombin aptamer. Therefore, the anticoagulated blood can be collected depending on the monitoring object.

The drug tube 12 connected to the thrombus formation chamber 10 can be made using a transparent glass, a thermoplastic resin, or the like. The end of the drug tube 12, which is opposite to the other side thereof connecting to the thrombus formation chamber 10, is connected to a syringe 21 for supplying a drug releasing the anticoagulation treatment or a drug promoting blood coagulation. The syringe 21 may be connected to a pump 31 and a pressing means (not shown) so that the plunger of the syringe 21 can be pressed at predetermined pressure. The pump may be a general pump commercially available. Alternatively, the pump may be a syringe pump constructed by extruding the syringe with air at a predetermined pressure, or inverting the syringe so that the plunger is on the top side, and placing a weight on a plunger. The drug tube 12 is filled with an anticoagulation releasing agent or a coagulation promoting agent, as described later.

For carrying out monitoring the thrombus with the apparatus for monitoring thrombus formation of the present invention, for example, the syringe 20 is filled with the whole blood or platelet plasma subjected to an anticoagulation treatment with a sodium citrate treatment (solution A). The syringe 21 is filled with a drug that releases the anticoagulation treatment, such as a calcium chloride solution (solution B). The solution A and the solution B are supplied into the inlet tube 11 by the pumps 30 and 31, respectively, so the solution B can reach to a concentration of 5 to 20 mmol at which the coagulation cascade of the solution A can be initiated. Subsequently, the solution A and the solution B are mixed in the inlet tube 11, so that the mixture is flown into the thrombus formation chamber 10. Further, for example, collagen or the like capable of inducing thrombus formation is previously applied on a part of the inside of the thrombus formation chamber 10 to form a thrombus inducing material. The thrombus formation chamber may be made using, for example, a transparent plastic tube. Thrombus formation can be easily monitored by an apparatus for monitoring the blood passing through such a transparently visible thrombus formation chamber 10.

The monitoring of thrombus formation can be evaluated with visual observation by flowing the blood for a predetermined period of time through a cell (thrombus formation chamber 10) treated with collagen and then removing the blood therefrom. When the pump for feeding the solution A and the solution B is air-driving, the solution A and the solution B may be fed at constant pressure. Therefore, thrombus formation on the collagen can be monitored by a decrease in flow rate of the blood discharged from the discharge tube 13. Alternatively, when a pressure gauge is mounted on the parts near the thrombus formation chamber 10 of the inlet tube 11 and the discharge tube 13, thrombus formation on the collagen can be monitored by observing a change in inner pressure of the thrombus formation chamber 10. Alternatively, it can be observed under microscope by providing the thrombus formation chamber 10 with a thickness of 500 µm or less. In particular, thrombus with platelet-rich plasma can be easily observed because it is highly visible and the thrombus formation thereof can be also observed by the naked eyes. Further, it is also possible to fluorescently label the blood platelets and monitor the fluorescence thereof with a fluorescence microscope by the method described in Patent Document 1.

Examples of the drug for releasing the anticoagulation treatment by a chelating agent such as citric acid include: calcium halides such as calcium chloride, calcium bromide, and calcium iodide; inorganic calcium salts such as calcium phosphate, calcium sulfate, calcium nitrate, and calcium bicarbonate; and calcium salts of organic acids such as formic acid, acetic acid, propionic acid, butyric acid, alginic acid, lactic acid, gluconic acid, glyceric acid, and glycerophosphoric acid, which are calcium compounds provided as free calcium donors.

The anticoagulation releasing agent can be selected and used depending on the coagulation-factor inhibitor when an anticoagulation treatment is carried out with a coagulation-factor inhibitor (anticoagulation treatment agent). For example, as an anticoagulation releasing agent when the anticoagulation treatment with heparin is carried out, protamine, heparinase or antiheparin antibody can be used. As an anticoagulation releasing agent when anticoagulation treatments are carried out with hirudin, hirulog, and aprotinin, anticoagulation releasing agent such as antihirudin antibody, antihirulog antibody, and antiaprotinin antibody, respectively, can be used.

Examples of the anticoagulation releasing agent when an anticoagulation treatment is carried out using antithrombin antibody as a coagulation-factor inhibitor include: a completely-inactivated thrombin such as a PPACK thrombin; the degradation fragment of thrombin, and a synthetic polypeptide containing an antibody-recognition epitope of thrombin.

The antibodies used in the anticoagulation treatment or the release of anticoagulation preferably include antibodies from which Fc domains are removed by papainase or the like to minimize the effects thereof on the complement system or antibodies such as chicken egg antibodies without the ability of activating the human complement system.

When a thrombin aptamer (Blood. 1993 Jun. 15; 81(12): 3271-6 or J Mol Biol. 1997 Oct. 10; 272(5): 688-98.), which is a single-strand oligo DNA, is used as an anticoagulation treatment agent, a substance that binds to the thrombin aptamer and inhibits the functions thereof, such as antisense DNA or antisense RNA, can be used as an anticoagulation releasing agent. When two kinds of thrombin aptamers, one recognizing exosite I and the other recognizing exosite II, are used in combination, an extremely higher effect of the anticoagulation treatment can be obtained in comparison with the case in which each of them is solely used. The antisense DNA used in this case may be one against part of the thrombin aptamer as long as it substantially inactivates the antithrombin function of the thrombin aptamer.

In addition, a fact that the thrombin aptamer and the antisense DNA thereof are effective as an anticoagulation treatment agent and an anticoagulation releasing agent, respectively, will be described with reference to reference examples as described below.

The coagulation system cannot be activated within several hours when an anticoagulation treatment is carried out with heparin. Thus, the blood can be stored for a long period of time in monitoring thrombus formation. However, for example, there is a case where the anticoagulation treatment is not suitable for examination of the blood collected from a patient subjected to heparin administration.

On the other hand, hirudin, hirulog, and antithrombin antibody are inhibitors for inhibiting the conversion of fibrinogen to fibrin by inhibiting thrombin which acts on the final stage of the coagulation system. However, a contact phase factor (such as pre-kallikrein or XII factor) of the coagulation cascade is gradually activated even in the case of completely inhibiting thrombin, so the activation of the upstream of the coagulation cascade can occur. Therefore, there is a case that it is not suitable for a prolonged storage of the blood.

Also, aprotinin inhibits the activity of kallikrein in the contact phase to delay the intrinsic blood coagulation cascade. However, the coagulation cascade is gradually activated even under the inhibition of kallikrein activity, so the blood is coagulated after several hours even in the presence of aprotinin.

Therefore, in the monitoring of thrombus formation of the blood after about several tens of minutes, it is possible to monitor the thrombus formation by anticoagulation treatment with the inhibitor of thrombin and/or aprotinin. However, it may be unpreferable in the case of requiring a long time to start the monitoring or requiring a long time for the monitoring.

When the thrombus formation is monitored after one hour or more from the blood sampling, an anticoagulation treatment may be carried out using a thrombin aptamer in combination with a maize-derived trypsin inhibitor, hirudin, and aprotinin. Alternatively, a small amount of heparin, for example, less than 1 unit/ml, which is a level that does not have a great influence on the coagulation time, may be used in combination with an inhibitor of contact phase factor or a thrombin inhibitor.

An extremely higher effect of the anticoagulation treatment can be obtained when a thrombin aptamer is used in combination with two kinds of aptamers for exosite I and exosite II. Further, the antisense DNAs of the respective aptamers can release the anticoagulation treatment, immediately.

Also, an inhibitor of contact phase factor, such as a maize-derived trypsin inhibitor (XII factor inhibitor) or aprotinin (kallikrein inhibitor), and an inhibitor of thrombin, such as a thrombin aptamer, are added to a sample (blood) in advance and then added with the antisense DNA of the thrombin aptamer (thrombin aptamer inhibitor) or the like. Thus, the function of the thrombin inhibitor alone is inhibited to release the functional inhibition of thrombin, followed by quickly flowing the sample into the thrombus formation chamber. As a result, for example, an extrinsic coagulation cascade can be activated by a tissue factor (tissue thromboplastin) or the like, so the blood coagulation is promoted and the physiological thrombus formation can be monitored.

Alternatively, anticoagulation treatments may be carried out with both the maize-derived trypsin inhibitor and the anticoagulation treatment agent which are capable of releasing an anticoagulation treatment, such as a chelator (citric acid), heparin, or the like; and then a free calcium donor such as calcium chloride, or heparinase may be allowed to release the corresponding anticoagulation treatments, followed by allowing the blood to be flown into a thrombus forming chamber to promote blood coagulation by activation of the extrinsic coagulation cascade.

In this case, a thrombus inducing material may preferably contain an appropriate amount of a tissue factor (tissue thromboplastin). Particularly preferably, the thrombus inducing material may be coated with a mixture prepared by mixing collagen with tissue thromboplastin and then drying because thrombus formation is promoted only in the thrombus formation chamber. When a thrombus inducing material coated with a collagen solution containing a tissue factor (tissue thromboplastin) as an atheromatous thrombus model is used, monitoring that reflects a pathological mechanism can be carried out.

Figure 9:
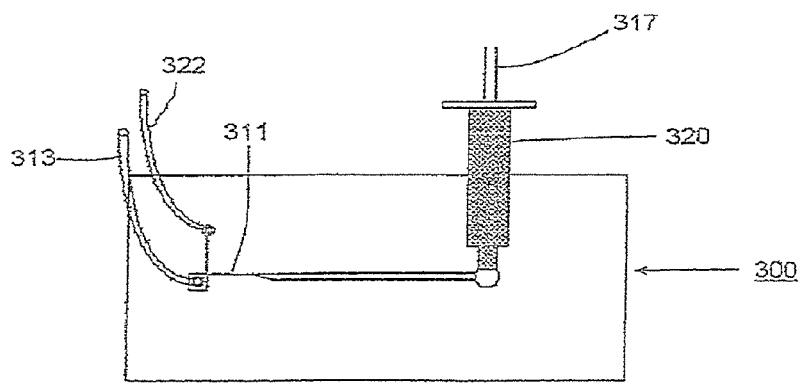
FIG. 9 are schematic diagrams illustrating main parts of an apparatus for monitoring thrombus formation of another example according to a third embodiment of the present invention, where FIG. 9 (A) illustrates a completion drawing, FIG. 9 (B) illustrates a main body of a microchip, and (C) illustrates a cover of the microchip.
Figure 9:
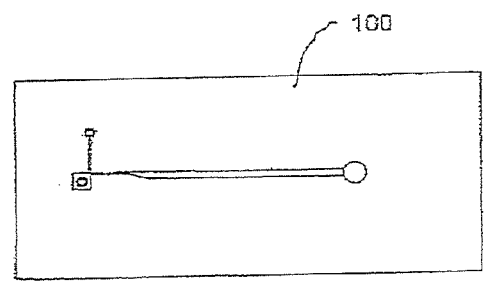
Figure 9:
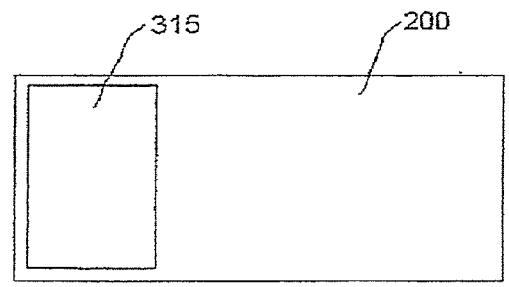

In addition, the thrombus formation can be monitored by adding the free calcium donor and the trypsin inhibitor to the blood subjected to the anticoagulation treatment with the calcium chelator such as citric acid, and quickly flowing the blood into the thrombus formation chamber, or by adding heparinase and trypsin inhibitor to the blood subjected to the anticoagulation treatment with heparin, and then quickly flowing the blood into the thrombus formation chamber. The method as described above, in which thrombus is monitored by mixing the anticoagulated blood obtained using one kind or more kinds of anticoagulation treatment agents with at least one anticoagulation treatment releasing agent corresponding to the anticoagulation agent used and then quickly flowing the blood into the thrombus formation chamber, may employ an apparatus for monitoring thrombus formation as illustrated in FIG. 9 as described below.

The above-mentioned thrombin inhibitors, such as hirudin and thrombin aptamers, synthesized low molecular inhibitors of contact phase factor, and anticoagulation treatment agents of protein are expensive compared with any of anticoagulation treatment agents such as citric acid and EDTA, which form chelates with calcium and the like. However, they do not change the concentrations of divalent metal ions such as calcium, magnesium, and zinc, so thrombus formation with the original concentrations of these ions in the patient's blood can be reflected to the monitoring. Therefore, the monitoring that more reflects the clinical condition of the patient becomes possible.

Blood coagulation can be suppressed by the inhibition of a contact phase factor such as activated factor XII or kallikrein. However, it has been reported that the activation of XIIa and kallikrein does not contribute very much to the actual physiological thrombus or hemostasis. Actually, there is no finding of hemorrhage or the like even in a patient with congenital deficiency of factor XII, pre-kallikrein, or the like at all. Particularly, in atherothrombosis such as myocardial infarction, it is widely known that the coagulation system is activated by a tissue factor due to plaque caused by the arteriosclerosis. Factor XII can be activated mainly by thrombin on the activated platelet. Therefore, in performing an anticoagulation treatment, when an inhibitor for inhibiting the activation of factor XII or prekallikrein or an inhibitor for inhibiting activated factor XII or kallikrein is used as an anticoagulation agent, there is no need to add the anticoagulation releasing agent. By adding any substance that activates extrinsic coagulation, such as a tissue factor (e.g., tissue thromboplastin), or a thrombus inducing material to the blood instead of the anticoagulation treatment agent or by adding the substance to the thrombus inducing material, the coagulation system is activated in an alternative pathway that avoids the XII-factor activation and the kallikrein activation to promote blood coagulation, so thrombus can be monitored in the thrombus formation chamber.

As anticoagulation treatment agents, which can be used in monitoring the thrombus formation after promoting blood coagulation by the addition of a substance that activates extrinsic coagulation, such as a tissue factor without adding the anticoagulation releasing agent, synthesized low molecular inhibitors such as the Kallikrein inhibitor PKSI-527 (Thromb Res 57: 889, 1990) and D-Phe-Arg-CK which is the activated factor XII inhibitor (Cal Biochem, Co., Ltd.) are exemplified. In addition, the protein inhibitors include antibodies against contact-phase protease in the coagulation cascade, such as anti-kallikrein antibody, anti-prekallikrein antibody, anti-coagulation factor XII antibody, anti-activated coagulation factor XII antibody, and maize-derived trypsin inhibitor.

For monitoring the thrombus formation after promoting blood coagulation by the addition of a substance that activates extrinsic coagulation without the addition of the anticoagulation releasing agent, particularly from the viewpoints of availability and anticoagulation ability, it is preferable that the blood is once subjected to an anticoagulation treatment with a combination of citric acid and maize-derived trypsin inhibitor or a combination of thrombin aptamer and maize-derived trypsin inhibitor, and the blood is stored thereafter, because the degree of freedom of monitoring operation can be heightened. Further, just before thrombus monitoring, an anticoagulation treatment with a maize-derived trypsin inhibitor is maintained while another anticoagulation treatment is partially released by a free calcium donor or the antisense DNA of a thrombin aptamer. In this case, as a model of atheromatous thrombus, it is preferable to activate extrinsic coagulation by using a thrombus inducing material coated with collagen or collagen containing tissue thromboplastin to promote blood coagulation.

Containers used in the thrombus monitoring, such as a syringe for supplying the blood and a vacuum blood-collecting vessel, are preferably coated with heparin or with a material having antithrombus ability and blood compatibility, such as polyvinyl lactoamide (PVLA) or poly-2-methoxyethyl acrylate (PMEA).

In an apparatus for monitoring thrombus formation according to another embodiment of the present invention, a tube and a thrombus formation chamber may be integrated with each other on a substrate by a fine channel such as a microchip.

Figure 4:
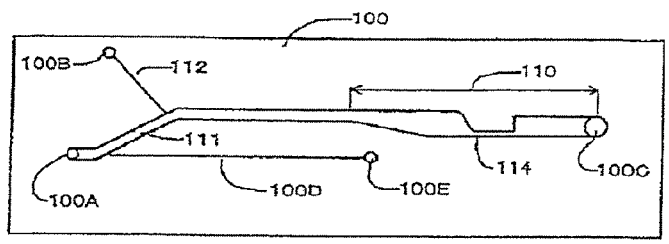
FIG. 4 is a schematic diagram illustrating a main part of an apparatus for monitoring thrombus formation (main body of a microchip) according to a second embodiment of the present invention.

FIG. 4 is a plane view of a main part of an apparatus for monitoring thrombus formation according to a second aspect of the present invention. In FIG. 4, a substrate 100 is grooved and a circuit is formed thereon. This embodiment is configured as follows. On a small substrate, a thrombus formation chamber as a main part of the apparatus for monitoring thrombus formation, an inlet tube which is connected to the thrombus formation chamber and through which blood is flown into the thrombus formation chamber, and a drug tube which is connected to the inlet tube and through which an anticoagulation releasing agent or a drug promoting blood coagulation is introduced into the thrombus formation chamber are integrated with each other and provided as a microchip circuit. In this embodiment, parts other than the main part, which are integrated on the substrate are the same as those of the first embodiment.

In FIG. 4, a substrate 100 is a main body of a microchip and the materials thereof may be any of metal, glass, plastic, silicone, and the like. In the light of observing a thrombus or the like, a transparent material is preferable. In the light of forming a circuit, a plastic material is preferable. Therefore, a transparent plastic material is particularly preferable. When it is made of silicon resin, such as polydimethyl siloxane (PDMS), the adhesiveness thereof is excellent. Thus, the circuit can be formed by contact bonding with a cover without adhesive or the like. When a substrate made of polystyrene is used, the channel can be easily coated with PVLA and subjected to an antithrombus treatment. Further, PMEA may also allow a simple, effective antithrombus treatment (see Reference Example 4).

Figure 5:
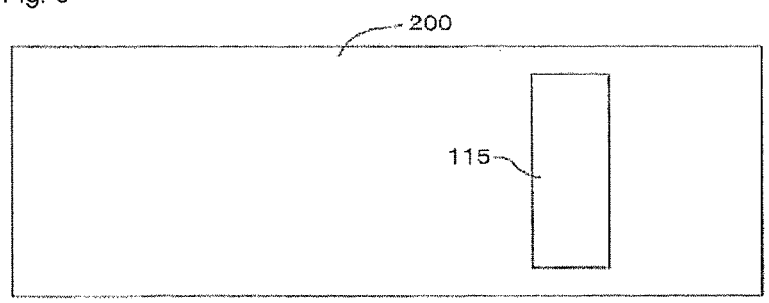
FIG. 5 is a schematic diagram illustrating a main part of the apparatus for monitoring thrombus formation (cover of a microchip) according to the second embodiment of the present invention.

FIG. 5 is a plane view of a substrate to be provided as a cover of the microchip which is overlapped and bonded to the substrate 100 of FIG. 4. A substrate 200 of FIG. 5 is a transparent slide glass or a plate or a sheet that are formed of plastic or the like. A substrate 200 is provided as a cover, and is overlapped and bonded to the substrate 100, so the circuit of the substrate can be formed of a thrombus formation chamber 110, an inlet tube 111, and a drug tube 112.

For providing the inner surface of the thrombus formation chamber 110 with a thrombus inducing material 115, for example, collagen or the like may be applied on the predetermined setting position of the substrate 200. An apparatus for monitoring thrombus formation having a thrombus formation chamber can be obtained when the substrate 100 and the substrate 200 are bonded to each other by joining or fitting while directing the collagen-applied surface of the substrate 200 inward. Because of simple application, collagen may be preferably applied to the flat substrate 200 having no groove. In addition, tissue thromboplastin is preferably applied after mixing with collagen, because a thrombus inducing material having a higher thrombus-inducing ability can be obtained.

Further, for easily thrombus formation with applied collagen, the glass having the collagen-applied portion may be subjected to the additional treatment, such as replacing the glass with a frosted glass or the like so that the surface area can be increased.

A connection part 100A, the connection part 100B, and the connection part 100C of the substrate 100 are connected to tubes (not shown) that form parts of the inlet tube, the drug tube, and the discharge tube, respectively. Thus, the connection part 100A and the connection part 100B are each connected to pumps (not shown) through the tubes. The anticoagulated blood is injected from the connection part 100A, and the anticoagulation releasing agent corresponding to the anticoagulation treatment agent is injected from the connection part 100B.

According to this embodiment, thrombus formation can be monitored with an extremely small amount of blood, thus the burden of the subject can be made small. In addition, platelets attached on the substrate 200 from the substrate 200 side can be monitored by labeling the platelets with a fluorescence reagent, such as mepacrine.

Further, the circuit 100D has a sealable end in which air is blocked. Thus, the circuit 100D is provided as a pressure gauge. The end of the circuit 100D may be preferably provided with a regulation valve 100E for relieving pressure or increasing sensitivity when the circuit 100D is provided as a pressure gauge. The regulation valve 100E can be closed by a cap or an adhesion tape and the volume thereof can be changed with packing such as resin depending on the required sensitivity. The circuit 100D is formed narrow so as to prevent the blood from mixing with air and prevent air from escaping. A thickness of the circuit 100D depends on the material of the substrate 100, but is about 0.1 mm to 0.5 mm. If the inner pressure of the inlet tube 111 of the apparatus for monitoring thrombus formation is increased by thrombus formation, the air in the circuit 100D is compressed by the blood, so the anticoagualted blood can be introduced into the circuit 100D by just that much. The inner pressure can be monitored by movement of the blood in the circuit 100D at any time.

The adhesion of platelets to collagen, the activation of the coagulation system on the activated platelets, and the accumulation of activated platelets by the platelet agglutination can be monitored by the apparatus for monitoring thrombus formation and/or the method of monitoring thrombus formation of the present invention, respectively.

Further, for reproducing the thrombus formation of atherothrombosis, constriction portions 14 and 114 are formed on the thrombus formation chambers 10 and 110, respectively. Therefore, the monitoring, which also reflects a high shearing-stress creating platelet agglutination, can be monitored.

FIG. 9 are schematic diagrams representing the main part of an apparatus for monitoring thrombus formation according to a third embodiment of the present invention. FIG. 9 describe a blood coagulation inhibitor inlet tube 322 and a pressure inlet tube 317, which mixes the blood coagulation inhibitor with the blood located downstream of the thrombus formation chamber. In this embodiment, the drug tube is not provided upper stream of the thrombus formation chamber.

According to the third embodiment, the blood collected after the addition of anticoagulation treatment agents (e.g., citric acid and maize-derived trypsin inhibitor) is further added with an anticoagulation releasing agent (e.g., free calcium donor) just before the measurement and then introduced into a syringe 320. Subsequently, a liquid for pressure-filling the blood, such as mineral oil, is pressed into the syringe from a pressure inlet tube 317 connected to the syringe 320, thereby extruding the blood to a microchip 300.

An increase in pressure exerted on the sample syringe 320 shows an occluded state of the channel with thrombus formation, so the monitoring of thrombus formation with a change in pressure is particularly suitable for the monitoring a model of strong atheromatous thrombus in which an obstructive thrombus is formed. The thrombus inducing material may be, but not specifically limited to, one prepared from collagen and a tissue factor. For example, such a thrombus inducing material is effective to the monitoring of thrombus when blood coagulation is promoted by activating extrinsic coagulation.

At the time of pressure measurement, for a more correct measurement of pressure in the channel with thrombus formation, as shown in FIG. 9, a blood coagulation inhibitor is introduced by the blood coagulation inhibitor inlet tube 322 and mixed with the blood located downstream of the thrombus formation chamber through a channel formed in the microchip 300. Thus, the blood in the channel subsequent to the thrombus formation chamber can be prevented from thrombus formation. Therefore, such a configuration is preferable because a change in pressure in the channel, which is due to constriction or closure of the channel with thrombus formation in the thrombus formation chamber, can be specifically, exactly measured.

Such a blood coagulation inhibitor may be preferably, but not specifically limited to, the anticoagulation treatment agent used in the present invention. In consideration of cost effectiveness and handleability, it is preferable to suitably select any of those that prevent blood coagulation by albuminoidal deformation, including an alkali or acidic solution, alcohol, urea, and SDSs.

Here, in the embodiment illustrated in FIG. 9, the apparatus for monitoring thrombus formation of the present invention comprises a suction pump provided on a discharge tube 313 instead of a pressure inlet tube 317, so the apparatus can determine the degree of thrombus formation on the basis of a change in suction pressure (negative pressure). Such a configuration may lead to a more efficient measurement while preventing the occurrence of a situation that a liquid for pressure-feeding of mineral oil or the like are mixed with the blood in a contact region and the mixture is fed, when the amount of the blood is small in the case of using a pump that indirectly extrudes the blood via a liquid separated in a layer as described later.

Further, there is no need of using a closed container such as a syringe as a container (sample tank) for supplying the blood into the apparatus for monitoring thrombus formation of the present invention. Thus, the container may have no cover and may be opened to the air. As a result, the apparatus for monitoring thrombus formation can be simplified. Further, in the apparatus for monitoring thrombus formation of the present invention, the inner pressure of the cannel is negative. Thus, when the apparatus for monitoring thrombus formation of the present invention is prepared from a microchip, for example, even in the case of an incomplete adhesion between the main body of the microchip and the cover of the microchip, there is no leak of the blood at all. In some cases, it may be directly used as an apparatus for monitoring thrombus formation only by fitting the main body of the microchip and the cover of the microchip together as long as the fitting is accurate.

Figure 10:
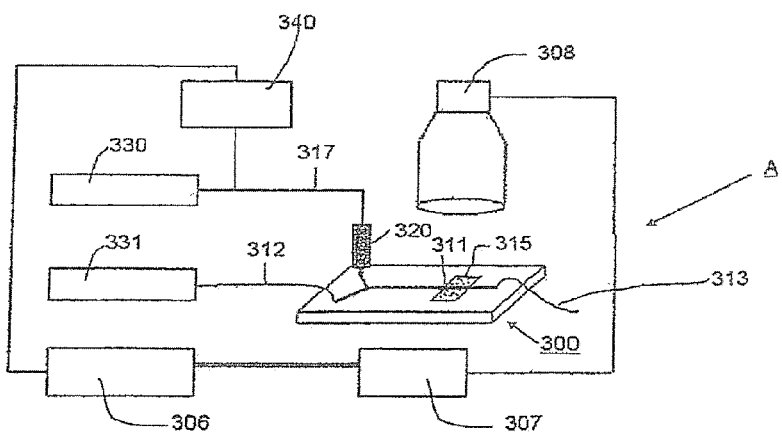
FIG. 10 is a schematic diagram illustrating a thrombus-monitoring system systemized using the apparatus for monitoring thrombus formation of the present invention.

FIG. 10 illustrates a further systematized thrombus-monitoring system A.

The thrombus-monitoring system A of FIG. 10 fills a micro-feeding pump 330 with a liquid having a density smaller than the blood. Then, the liquid is pressed into a sample syringe 320 in which the blood is placed by a pressure inlet tube 317 and then layered on the blood, thereby extruding the blood into a microchip 300. The extruded blood is mixed with anticoagulation releasing agent injected from a drug tube 312, followed by reaching to a thrombus formation chamber 311. A liquid for pumping the blood in a micro-feeding pump 330 may be any of oils and fats, such as liquid paraffin, mineral oil, and silicone oil, and a normal saline solution. In this way, it becomes possible to prevent both the micro-feeding pump 330 and a pressure sensor 340 from being polluted with the blood by indirectly extruding the blood.

Further, such a pump for indirectly extruding the blood by the liquid being separated in a layer with respect to the blood can be employed in the apparatus for monitoring thrombus formation according to any of the embodiments of the present invention.

Further, the pressure sensor 340 can determine the pressure applied on the sample syringe 320 by the micro-feeding pump 330.

Further, in this thrombus-monitoring system A, the state of thrombus formation can be recognized in more detail by an image analysis. In particular, in the case of labeling platelets and white blood cells with quinacrine and then monitoring the adhesion and the agglutination thereof to collagen, luminance per unit area due to the fluorescence color development is monitored by an image analysis. Thus, the results of the monitoring can be evaluated and stored as data. The image analysis can be carried out by processing an image captured by a fluorescent stereoscopic microscope 308 with a CCD camera by a computer 307 and representing the image on a display.

Therefore, in the thrombus-monitoring system A, it is possible to determine a comprehensive state of thrombus formation from the results of the image analysis and a change in pressure applied on the sample syringe 320.

Further, such a thrombus-monitoring system can be systematized using the apparatus for monitoring thrombus formation of any of the embodiments of the present invention.

Figure 12:
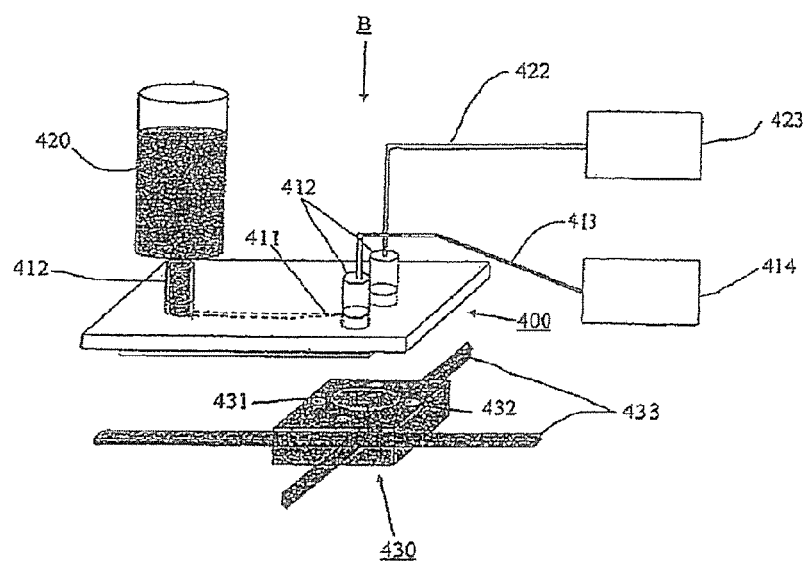
FIG. 12 are schematic diagrams illustrating main parts of an apparatus for monitoring thrombus formation according to a fourth embodiment of the present invention, where FIG. 12 (A) illustrates a completion drawing, FIG. 12 (B) illustrates a cover of a microchip, and FIG. 12 (C) illustrates a substrate of the microchip.
Figure 12:
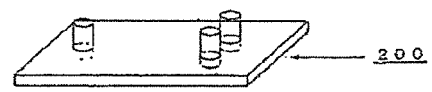
Figure 12:

FIG. 12 are schematic diagrams illustrating an apparatus for monitoring thrombus formation of a fourth embodiment of the present invention. The apparatus for monitoring thrombus formation is provided with a camera for the observation of thrombus formation.

In the apparatus for monitoring thrombus formation, for example, the blood which is anticoagulated with citric acid and a maize-derived trypsin inhibitor is added with an anticoagulation treatment releasing agent (e.g., free calcium donor) and quickly filled in a syringe 420. The syringe 420 is aspirated by a pump 414 connected to a discharge tube 413 to allow the blood to pass through a thrombus formation chamber 411, thereby forming a thrombus. The degree of thrombus formation can be determined by the change in the suction pressure (negative pressure).

Also, for preventing the blood after passing through the thrombus formation chamber from coagulating to thereby clogging a discharge tube 413, or from affecting on a pressure measurement, a thrombus formation inhibitor inlet tube 422 mixes a thrombus formation inhibitor with the blood after passing through the thrombus formation chamber.

Further, a camera 430 (e.g., CCD camera) is arranged under the microchip 400 to take an image of the thrombus formation chamber, so the space above the microchip can be effectively used. A rail 433 is able to move the camera 430 back and forth and around under the thrombus formation chamber. By using the camera 430 which has a function of storing its position quantified as the X-axis and the Y-axis, it can take images while regularly moving around a plurality of specific points. As configured above, it is possible to monitor the process of thrombus formation with time over a wide area of the thrombus formation chamber 411 even the magnification of the camera 430 is set to a high level. Further, an optical source 432 (e.g., LED) is preferably located around the camera 430 as the optical source 432 can be simultaneously moved while keeping its positional relationship with the camera 430. It is preferable that the optical source 432 is able to irradiate the light at a wavelength that can excite a specific fluorescent substance together with white light depending on a fluorescent material to be provided as an imaging target, thereby allowing the excitation of various fluorescent materials.

EXAMPLES

Hereinafter, the present invention will be described in detail with specific examples. However, the present invention is not limited to these examples.

Example 1

An apparatus for monitoring thrombus formation illustrated in FIG. 1 is used to fill a syringe 20 with 50 ml of a citrate-treated blood (solution A) in which 9 parts by volume of the blood immediately after the blood sample is mixed with 1 part by volume of 3.2% sodium citrate, and to fill a syringe 21 with 10 ml of 0.2M $CaCl_2$ (solution B). The syringes 20 and 21 are connected to transparent nylon tubes (inlet tube 11 and drug tube 12) with an inner diameter of 3 mm. Both tubes are joined together at a T-shaped joint (cheese) and then connected to a polycarbonate thrombus formation chamber 10 of 3 mm in inner diameter and 1 cm in length through a single nylon tube (inlet tube 11) of 3 mm in inner diameter and 3 cm in length. The thrombus formation chamber 10 itself is constructed as a removable cassette. The joint portion between the cassette and the nylon tube (inlet tube 11) is made liquid-tight via an O-ring made of silicon rubber. A glass member is fixed on the inside of the cassette by an epoxy-based adhesive, thereby forming a constriction portion 14. The constriction portion 14 is designed so that the most narrowed site of the constriction portion 14 may have an inner diameter (the maximum gap between the constriction portion 14 and the inner wall) of 1.5 mm. In addition, the thrombus formation chamber 10 is connected liquid-tight with a tube as a discharge tube 13 having the same diameter and formed of the same material through an O-ring made of silicon rubber, and thus a thrombus monitoring apparatus 1 as illustrated in FIG. 1 is manufactured. Note that flange-type pressure gauges 40 and 41 are mounted on parts of the inlet tube 11 and the discharge tube 13 near the thrombus formation chamber 10 via joints (cheeses), respectively. In addition, the glass material of the constriction portion on the inner surface of the thrombus formation chamber 10 is prepared such that collagen is coated as a thrombus inducing material 15 on the glass constriction portion on the inside by immersing in a 0.1 N acetic acid solution containing 1% insoluble collagen type I (manufactured by Wako Pure Chemical Industries, Ltd.) and then drying. The syringes 20 and 21 are inverted so that plunger are on the top side and weights are then placed on the plungers so as to allow the solution A and the solution B to be flown at 5 ml/min and at 0.5 ml/min, respectively, to be syringe pumps.

When the solution A and the solution B are flown for 10 minutes, a difference between the pressure gauges 40 and 41 of the inlet tube 11 and the discharge tube 13 is emerged after several minutes and such a difference is then increased with time. Simultaneously, it is confirmed that the blood discharged from the discharge tube 13 is also gradually decreased. When the flow of all solutions is completed, a physiological saline solution is flown into the apparatus for monitoring thrombus formation 1 to wash the thrombus formation chamber 10. Thus, the formation of thrombus can be found in the thrombus formation chamber 10 by visual observation.

Example 2

An apparatus for monitoring thrombus formation 1 is prepared and thrombus formation is then monitored in a manner similar to Example 1, except that the solution A of Example 1 is further added with an unfractionated heparin (prepared from pig mucous) at a concentration of 1 mg/ml.

In this case, there is no pressure difference and no decrease in blood flow occurred, and thrombus cannot be found in the thrombus formation chamber 10 by visual observation after washing with a physiological saline solution.

Example 3

Figure 2:
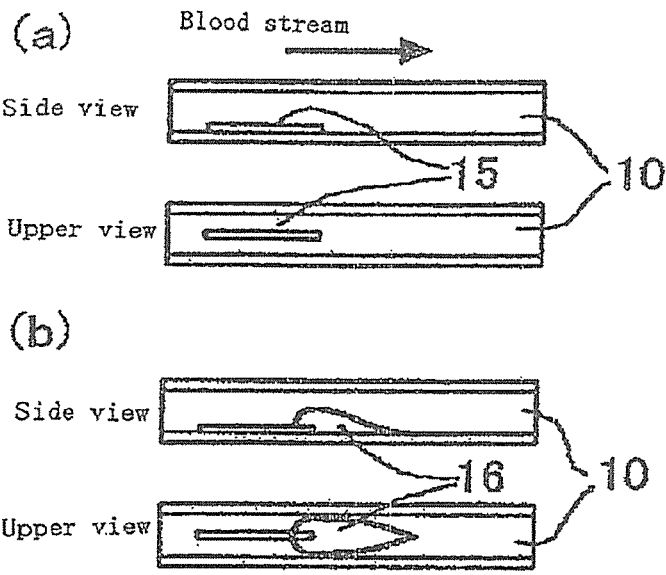
FIG. 2 (*a*) is a schematic diagram illustrating installation conditions of a thrombus inducing material 15 of Examples 3, 5, and 6 according to the first embodiment of the present invention, and FIG. 2 (*b*) is a schematic diagram illustrating results of thrombus formation of Examples 3, 5, and 6 according to the first embodiment of the present invention.

An apparatus for monitoring thrombus formation 1 was prepared in a manner similar to Example 1 with the exceptions that: a glass tube of 3 mm in diameter and 5 cm in length was provided as a cassette type thrombus formation chamber 10; the syringes 20 and 21 were each connected to syringe pumps driven by electric motors; and, instead of the constriction portion 14 and the collagen coated as a thrombus inducing material 15 on the constriction portion 14, as shown in FIG. 2(a), silk of 1.5 cm in length immersed in collagen of Example 1 and air dried at 4° C. were attached by an adhesive as a thrombus inducing material 15 on the inner surface of the thrombus formation chamber 10 which is 5 mm inside from the connection part of the glass tube and the inlet tube 11.

After flowing the solution A in the syringe 20 at 3 ml/min and the solution B in the syringe 21 at 0.3 ml/min for 15 minutes, the thrombus formation chamber 10 was detached and the inside thereof was then washed with a physiological saline solution. As a result, visual observation confirmed that thrombus 16 with a length of about 1 cm and a thickness of about 1 mm in the form of a comet shape as shown in FIG. 2(b), which seems to be formed from the downstream side of the silk as a starting point and extend to the downstream was attached on the inner surface of the glass tube. Here, it is considered that the influence of blood flow may cause the thrombus in a cornet shape.

The widest part of the thrombus had a width of about 3 mm.

Example 4

Figure 3:
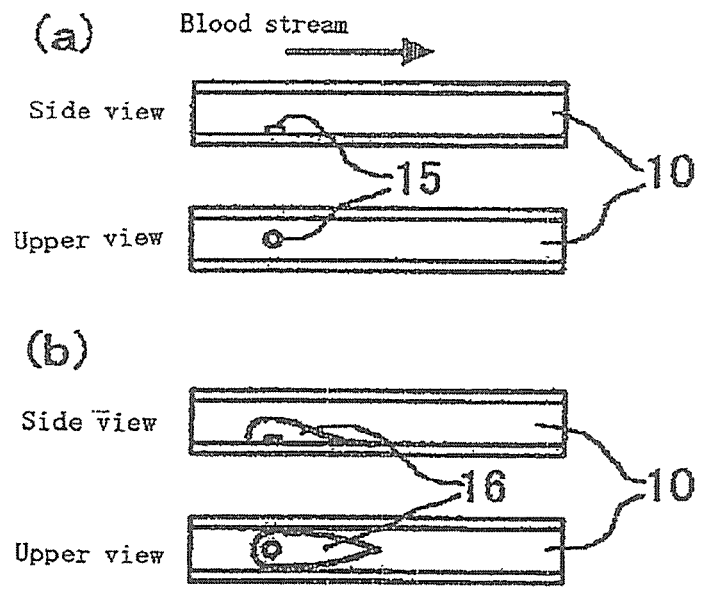
FIG. 3 (*a*) is a schematic diagram illustrating installation conditions of the thrombus inducing material 15 of Example 4 of the first embodiment of the present invention, and FIG. 3 (*b*) is a schematic diagram illustrating results of thrombus formation of Example 4 according to the first embodiment of the present invention.

An apparatus for monitoring thrombus formation 1 was prepared in a manner similar to Example 3 with the exception that, instead of silk, as shown in FIG. 3(a), 50 µl of the blood without an anticoagulation treatment was dropped on the inner surface of a glass tube by a Pasteur pipette and then left standing at room temperature for 15 minutes, thereby obtaining a disk-shaped thrombus with a diameter of about 2 mm as a thrombus inducing material 15.

In a manner similar to Example 3, after flowing the solution A and the solution B, the thrombus formation chamber 10 was removed and then the inside thereof was washed with a physiological saline solution. As a result, visual observation confirmed that thrombus 16 with a length of about 1 cm and a thickness of about 1 mm in the form of a comet shape as shown in FIG. 3(b) extending toward the downstream while wrapping around thrombus as a thrombus inducing material 15 was attached on the inner surface of the glass tube. Here, it is considered that the influence of blood flow may cause the generated thrombus in a comet shape.

The widest part of the thrombus had a width of about 3 mm.

Example 5

An apparatus for monitoring thrombus formation 1 was prepared and thrombus formation was then monitored in a manner similar to Example 3 with the exception that the solution A was further added with Argatroban (registered mark, manufactured by Daiichi Pharmaceutical Co., Ltd.) as an anticoagulation treatment agent at a concentration of 0.1 mg/ml with respect to the solution A of Example 3.

As a result, visual observation did not confirm the presence of thrombus in a glass tube after washing with the physiological saline solution.

Example 6

An apparatus 1 for monitoring thrombus formation is prepared and thrombus formation is then monitored in a manner similar to Example 3 with the exceptions that the anticoagulated blood prepared by the addition of hirudin at a concentration of 1 μg/ml with respect to the whole blood is used as the solution A and antihirudin polyclonal antibody (manufactured by COSMO BIO CO., LTD.) dissolved at a concentration of 1 mg/ml in a physiological saline solution with respect to the whole blood is used as the solution B.

In this case, almost the same thrombus formation is confirmed as that of Example 3.

Example 7

There are prepared 10 ml of the whole blood (solution A) which was subjected to an anticoagulation treatment by adding to the blood immediately after the blood sampling 10 μg/ml of aprotinin and 1 μg/ml of recombinant hirudin (manufactured by Wako Pure Chemical Industries, Ltd.); and 1 ml of a solution (solution B) which was prepared by adding an antihirudin polyclonal antibody (manufactured by COSMO BIO CO., LTD.) from which a Fc domain was removed by a papain-immobilized resin to 1000-fold diluted physiological saline s solution of 1 vial/ml of thromboplastin reagent (manufactured by Sysmex Corporation) as a drug for promoting blood coagulation.

For manufacturing an apparatus for monitoring thrombus formation, a substrate 100 shown in FIG. 4, which is made of polydimethyl siloxane with a width of 40 mm, a length of 70 mm, and a thickness of 1.5 mm, and a substrate 200 shown in FIG. 5, which has a thickness of 1 mm and is made of glass with the same dimensions, are used.

A circuit containing a thrombus formation chamber 110 is formed by cutting a groove with a depth of 0.5 mm on the surface of a substrate 100 with a pattern shown in FIG. 4. The depth of the part of the groove to be provided as an inlet tube 111 is 1 mm. The length of the circuit 100D is 30 mm. A through hole of 1 mm in diameter is formed at the end of the groove and provided as a regulation value 100 E which is closed by an operable and closable cap. The thrombus formation chamber 110 has a length of 30 mm and a width of 2.5 mm at the wider portion and a constriction portion 114 having a width of 0.5 mm. Then, a through hole with a diameter of 1 mm is provided as each of the connection parts 100A and 100B. In addition, a through hole with a diameter of 2.5 mm is provided as a connection part 100C.

Collagen in the form of a band with a width of 10 mm is applied as a thrombus inducing material 115 to the substrate 200 at a position covering the constriction portion 114 of the substrate 100 as shown in FIG. 5. The application of collagen is carried out such that the rectangular masking tape corresponding to the constriction portion 114 of the substrate 200 is attached and a silicone-based stripping agent SRX-211 (Dow Corning Toray Co., Ltd.) is then coated thereon. Subsequently, the masking tape is peeled off. Then, a solution of collagen type 1 (Wako Pure Chemical Industries, Ltd.) dissolved in 0.1N acetic acid is dropped so as to be 1% thereof on the glass region free of the stripping agent and then left standing for 1 hour at 25° C. After that, collagen on the stripping agent layer is washed out with purified water, and collagen is only applied to a rectangular glass region corresponding to the constriction portion 114, where the stripping agent is not applied.

Subsequently, the collagen-applied surface of the substrate 200 and the circuit-formed surface of the substrate 100 are bonded together face-to-face.

Connection parts 100A and 100B are connected to silicone tubes having an inner diameter of 1 mm from the back surface (circuit-free side) of the substrate 100 and then connected to a 10-ml syringe filled with the solution A and a 1-ml syringe filled with the solution B, respectively. These syringes are each attached to syringe pumps, respectively. Note that another connection part 100C is connected to a silicon tube having an inner diameter of 2.5 mm, which is provided as a discharge tube.

The solution A is injected from the connection part 100A at a flow rate of 0.3 ml/min. The solution B is injected from the connection part 100B at a flow rate of 0.03 ml/min.

Figure 6:
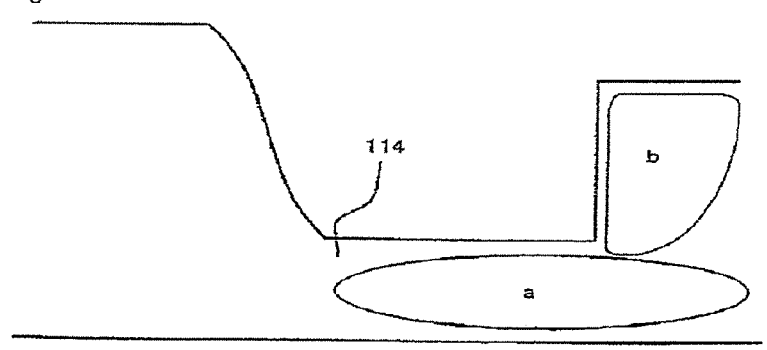
FIG. 6 is a schematic diagram illustrating the position of thrombus formation of Example 7 according to the second embodiment of the present invention.

The solution A and the solution B are allowed to run from the connection part 100A and the connection part 100B for 5 minutes, respectively. A physiological saline solution is injected from the connection part 100A to wash out the blood. As a result, thrombus formation is confirmed mainly on the region a and the region b of FIG. 6 on the collagen-treated surface of the substrate 200.

Example 8

Figure 7:
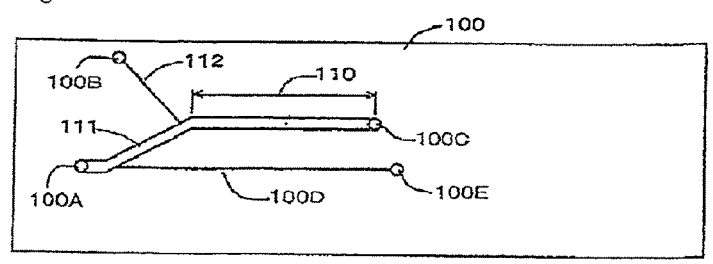
FIG. 7 is a schematic diagram illustrating a main part of an apparatus for monitoring thrombus formation of another example (main body of a microchip) according to the second embodiment of the present invention.
Figure 8:
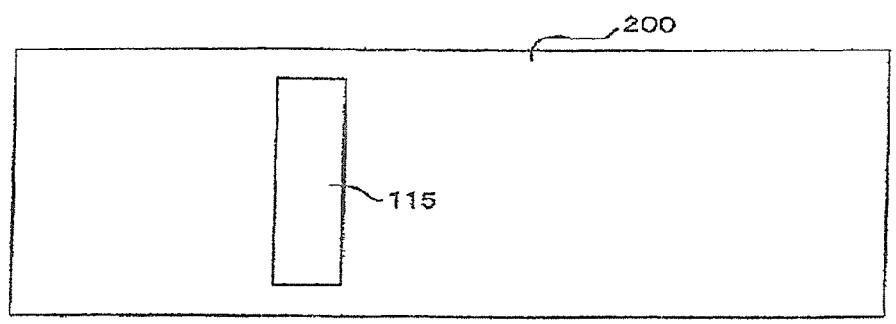
FIG. 8 is a schematic diagram illustrating a main part of the apparatus for monitoring thrombus formation (cover of a microchip) of another example according to the second embodiment of the present invention.

An apparatus for monitoring thrombus formation is prepared and thrombus formation is monitored in a manner similar to Example 7 with the following exceptions: solution A is prepared such that the blood immediately after blood sampling is added with anti-factor XII polyclonal antibody (manufactured by COSMO BIO CO., LTD.), from which a Fc domain is cut off by papain, at a concentration of 0.3 mg/ml and unfractionated heparin (pig origin, Wako Pure Chemical Industries, Ltd.) at a unit of 0.3; solution B is prepared by diluting a thromboplastin reagent (manufactured by Daiichi Pure Chemicals Co., Ltd.) 50 times; the application of collagen is carried out by pretreating the collagen-applied region of a transparent polystyrene substrate 200 (1 mm in thickness) shown in FIG. 8 with the dropping of a solution prepared by dissolving potassium permanganate in concentrated sulfuric acid at a concentration of 2 g/l, subjecting to reaction at 25° C. for 10 minutes followed by quickly washing with purified water, collagen is applied by dropping a solution in which collagen type 1 (Wako Pure Chemical Industries, Ltd.) dissolved in 0.1N acetic acid is dissolved at a concentration of 1% on the pretreated region, and leaving standing at 25° C. for 1 hour followed by washing out with purified water; and a substrate 100 without a constriction portion is used for the thrombus formation chamber 110 shown in FIG. 7. Note that the connection part 100C of the substrate 100 is provided for a through hole of 1 mm in diameter and connected to a silicone tube of 1 mm in inner diameter as a discharge tube.

After flowing the solution A and the solution B for 10 minutes, a physiological saline solution is injected from the connection part 100A to wash out the blood, thereby confirming the attachment of red thrombus on the channel part of the collagen-applied region of the substrate 200.

Example 9

An apparatus for monitoring thrombus formation was prepared and thrombus formation was monitored in a manner similar to Example 7 with the exceptions that:

a solution A was prepared such that the blood immediately after the blood sampling was subjected to an anticoagulation treatment by the addition of aprotinin at a concentration of 0.05 mg/ml and recombinant hirudin (manufactured by Wako Pure Chemical Industries, Ltd.) at a concentration of 1 µg/ml and then added with quinacrine (Sigma Co., Ltd.); and the connection part 100B is closed by a cap and only the solution A is then injected from the connection part 100A at a flow rate of 1 ml/min.

When observed with a fluorescence stereoscopic microscope focused on the collagen-applied surface from the substrate 200 side, a fluorescence color development of green quinacrine was confirmed on the portion of the collagen-applied surface and such a region spreads out in as macular region with time. After 10 minutes, the green fluorescence color development which may be due to thrombocytic adhesion was confirmed with the most of the collagen-applied surface.

Example 10

An apparatus for monitoring thrombus formation was prepared and thrombus formation was monitored in a manner similar to Example 9, except that solution A was prepared without the addition of quinalin.

The blood was injected from the connection part 100A at a flow rate of 1 ml/min. When the tube of the connection part 100C was pinched to close the tube for 2 seconds during the injection, the blood was moved up instantly to 20 mm from the branching point in the circuit 100D accompanied by an increase in inner pressure. Even after opening the connection part 100C, the blood does not move from the 20-mm point, so the evidence of an increase in pressure could be confirmed.

Example 11

An apparatus for monitoring thrombus formation is prepared and thrombus formation is monitored in a manner similar to Example 8 with the exceptions that: the antithrombin polyclonal antibody (COSMO BIO CO., LTD.) from which a Fc domain is removed by a papain is added so as to be in a concentration of 30 µg/ml instead of heparin of the solution A of Example 8; and the solution B of Example 8 is further added with PPACK thrombin in a concentration of 5 mg/ml.

After flowing the solution A and the solution B for 15 minutes, a physiological saline solution is injected from the connection part 100A to wash out the blood. As a result, it is confirmed that red thrombus is attached on a channel portion of the collagen-treated region of the substrate 200.

Example 12

An apparatus for monitoring thrombus formation was prepared and thrombus formation was monitored in a manner similar to Example 7 with the exception that:

solution A was prepared such that 50 ml of the blood immediately after the blood sampling, which was added with 0.5 units/ml of heparin and 10 µg/ml of aprotinin, was centrifuged at 800 rpm and platelet-rich plasma (PRP) was prepared from the supernatant, thereby obtaining the solution A; and a solution in which 1 vial/ml of a thromboplastin reagent (Sysmex Corporation) was diluted 30 times with a physiological saline solution was used as solution B.

A thrombus formation of the constriction portion 114 was monitored for 15 minutes using a stereoscopic microscope. A plurality of platelet clots attached on around the constriction portion 114 was confirmed. It was also monitored that the number of the clots increased while the sizes thereof also increased, with the platelet clots repeating attaching and detaching.

Example 13

Thrombus formation was monitored by running solution A and solution B in a manner similar to Example 7 with the following exceptions:

solution A was prepared by adding 500 µg of erythrocyte collected from the centrifuged sediment to 20 ml of PRP of the solution A of Example 12;

a solution in which 1 vial/ml of a thromboplastin reagent (Sysmex Corporation) diluted 30 times with a physiological saline solution was used as solution B;

a slide glass was prepared by coating the whole surface of the substrate 200 with a silicone-based stripping agent SRX-211 (Dow Corning Toray Co., Ltd.); and approximately 1 µl of the whole blood was attached on near the widening end point of a widening portion successively extending to 2.5 mm in width, which is adjacent to upstream of the constriction portion 114 of the thrombus formation chamber 110 on the substrate 100, then the whole blood was left standing at room temperature for 10 minutes to cause coagulation thereof, and a preliminary thrombus was formed to be used as a thrombus inducing material.

The thrombus-attached region was monitored by a stereoscopic microscope for 15 minutes. The formation of a new red thrombus, which was located downstream from the preliminary thrombus as an origin, was confirmed after about 5 minutes, gradually extended downstream up to 15 minutes, and the width thereof extended to 2.5 mm. It was confirmed that the blood flows along the formed thrombus or flows through the gaps between the formed thrombus.

Example 14

An apparatus for monitoring thrombus formation was prepared and thrombus formation was monitored in a manner similar to Example 7 with the following exceptions:

50 ml of blood immediately after the blood sampling added with an exosite I thrombin aptamer (GGTTGGTGTGGT-TGG: SEQ ID NO. 1) at a final concentration of 5 µM and a maize-derived trypsin inhibitor (COSMO BIO CO., LTD.) at a final concentration of 30 µg/ml was centrifuged at 800 rpm for 10 minutes, and platelet-rich plasma (PRP) was formed from the supernatant and provided as the solution A;

antisense DNA (CCAACCACACCAACC: SEQ ID NO. 2) was dissolved in a physiological saline solution so as to be 150 µM in concentration and provided as the solution B; and at the time of mounting a thrombus inhibitor 115, a solution, which was prepared by mixing the collagen solution of Example 7 with a solution prepared by dissolving 1 vial of thromboplastin reagent (Sysmex Corporation) in 1 ml of purified water and then dialyzed at a ratio of 5:1, was dropped onto a silicone-unapplied region and dried with air at 4° C.

A thrombus formation of the constriction portion 114 was monitored for 5 minutes using a stereoscopic microscope. A plurality of platelet clots attached around the constriction portion 114 was confirmed. It was also monitored that the number of the clots increased while the sizes thereof also increased, with the platelet clots repeating attaching and detaching.

Example 15

An apparatus for monitoring thrombus formation was prepared and thrombus formation was monitored in a manner similar to Example 14 with the following exceptions:

after preparing PRP by the same procedure as that of Example 14, antisense DNA (CCAACCACACCAACC: SEQ ID NO. 2) was added so as to be 15 µM in concentration immediately before the measurement, thereby releasing the anti-thrombin treatment and provided as the solution A;

the injection opening of the connection part 100B is closed in a manner similar to Example 9;

collagen type I (collagen reagent for coating a cell culture dish with collagen, Type I-A stock solution, Cellmatrix Co., Ltd.) was used instead of the collagen solution of Example 14; and only the solution A was flown at a flow rate of 0.2 ml/min. for 5 minutes.

A thrombus formation of the constriction portion 114 was monitored using a stereoscopic microscope. A plurality of platelet clots attached around the constriction portion 114 was confirmed. It was also monitored that the number of the clots increased while the sizes thereof increased, with the platelet clots repeating attaching and detaching.

Example 16

An apparatus for monitoring thrombus formation was prepared in a manner similar to Example 7 with the following exceptions:

a groove of 0.1 mm in depth was formed on the surface of the substrate by cutting in a pattern shown in FIG. 7, while leaving partition walls such that convex rows each having a length of 1 mm and a width of 40 µm were made stand on the whole surface of the bottom portion around the center of the thrombus formation chamber 110 with intervals of 40 µm therebetween;

the injection opening of the connection part 100B was closed in a manner similar to Example 9; and the substrate 200 was a simple slide glass without a surface treatment. The gap (channel) between the partition walls simulates a blood capillary.

The whole blood immediately after the blood sampling was subjected to an anticoagulation treatment by the addition of a maize-derived trypsin inhibitor with a final concentration of 30 µg/ml and an exosite I thrombin aptamer with a final concentration of 10 µM. Immediately before monitoring, antisense DNA of exosite I thrombin aptamer was added so as to be 30 µM in concentration, followed by injection from 100A at a flow rate of 0.05 ml/min for 5 minutes.

The thrombus formation in the gap between the partition walls was monitored using a stereoscopic microscope. As a result, the channels were closed in sequence during the monitoring for 5 minutes. It was monitored that about half of the channels were closed by thrombus formation.

Example 17

A syringe-type solution-feeding system shown in FIG. 9 was used. A microchip 300, where the substrate and the cover of the microchip shown in FIG. 9(B) and FIG. 9(C), respectively, made of the same materials as those of Example 7 were pressure-bonded, was used. The microchip 300 comprises a blood coagulation inhibitor inlet tube 322 and a discharge tube 313 which were connected to the substrate 100 as in the case with the discharge tube of Example 7. However, the grooves of the microchip 300 of FIG. 9 are all formed of 200 µm in depth. Also, a channel was formed such that the blood could be introduced into the channel from the sample syringe 320, while the channel had a width of 1 mm and a length of 40 mm and was connected to a thrombus formation chamber 311 composed of narrow channel having a width of 200 µm and a length of 10 mm and the blood coagulation inhibitor inlet tube 322. A solution was prepared such that 1 vial of the Sysmex Corporation PT reagent (tissue thromboplastin) was dissolved in 1 ml of purified water and then dialyzed in purified water, the dialyzed product in purified water was mixed with collagen type I (manufactured by Nitta Gelatin Inc.) at a ratio of 1:1. The solution was applied to the position of the thrombus inducing material 315 as shown in FIG. 9. After that, the applied portion was dried at 4° C. in air and thrombus formation chamber 311 was covered, which was used as a thrombus inducing material 315. The blood was collected after the addition of an anticoagulation treatment agent such that the final concentrations of the respective components in the syringe were 25 µg/ml for maize-derived trypsin inhibitor, 10 µM for exosite I thrombin aptamer, 10 µM for exosite II thrombin aptamer (5'-AGTCCGTGGTAGGGCAGGT-TGGGGTGACT-3': SEQ ID NO. 3). Immediately before monitoring, the blood thus collected was added with antisense DNAs with respect to thrombin aptamers of exosite I and exosite II so that each of them would reach to a concentration of 40 µM. Then, a syringe (1 ml syringe, manufactured by Terumo Corporation) was filled with the blood and provided as the sample syringe 320 shown in FIG. 9. The My Flow (manufactured by Arbiotec Co., Ltd), which is a microfeeding pump capable of monitoring the inner pressure of a liquid-feeding pump, was connected to a pressure inlet tube 317 shown in FIG. 9. Mineral oil was pressed into the microchip 300 from the top of the syringe 320 and the blood was pushed out into the microchip 300 at a flow rate of 50 µl/min, while the pressure exerted on the sample syringe 320 was monitored.

As a blood coagulation inhibitor, 1 M of Tris-HCl (pH 10) was flown from the blood coagulation inhibitor inlet tube 322 at a flow rate of 50 µl/min. Pressure began to rise 6 minutes after starting the pressure measurement.

Figure 13:
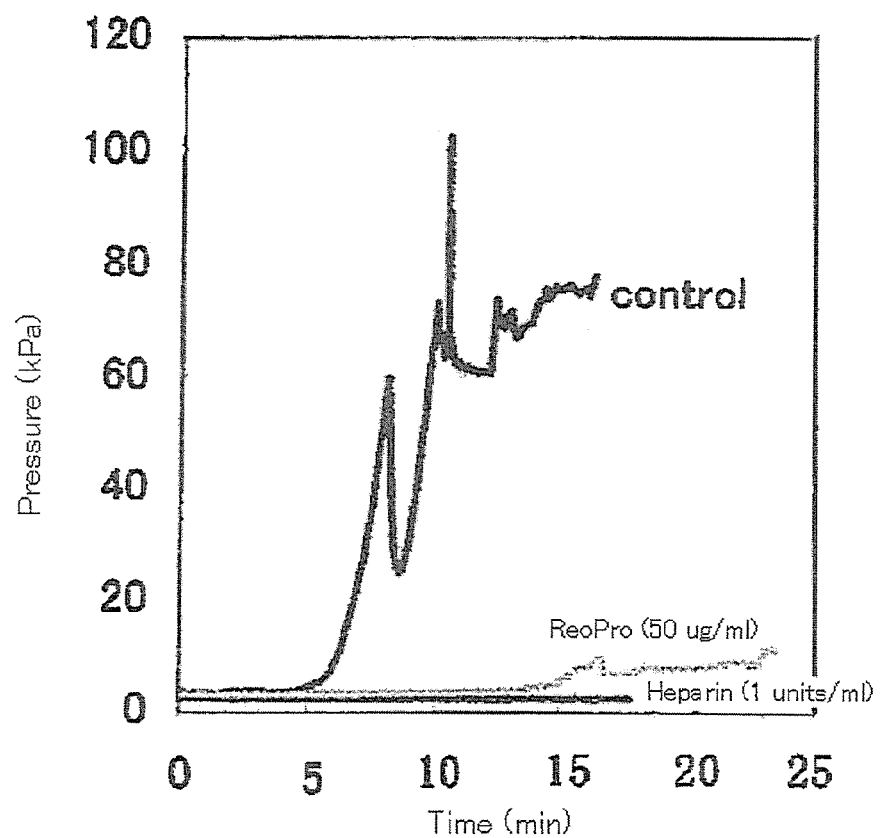
FIG. 13 is a graph showing results of pressure measurements of Example 17 (control), Example 18 (heparin), and Example 19 (Reopro).

The pressure, repeating the changes thereof up and down due to the movement of thrombus ("control" shown in FIG. 13), rose up to 80 kPa.

Example 18

The blood sampling was carried out with the addition of an anticoagulation treatment agent in manner similar to Example 17. Subsequently, the same procedure as that of Example 17 was carried out, except that unfractionated heparin was added at a concentration of 1 unit/ml. The measurement of pressure was then performed. The pressure began to rise 13 minutes after starting the measurement. The pressure rose up to about 10 kPa ("Heparin" shown in FIG. 13).

Example 19

The blood sampling was carried out with the addition of an anticoagulation treatment agent in manner similar to Example 17. Subsequently, the same procedure as that of Example 17 was carried out, except that ReoPro (LILLY Co., Ltd.) was added at a concentration of 50 μg/ml. The measurement of pressure was then performed. An increase in pressure could not be confirmed in the measurement for 18 minutes ("ReoPro" shown in FIG. 13).

Example 20

The blood sampling was carried out with the addition of 3.2% citric acid so that the ratio of citric acid and the blood be 1:9. Further, the blood was added with a maize-derived trypsin inhibitor at a concentration of 25 μg/ml to carry out an anticoagulation reaction. Immediately after adding calcium chloride to the anticoagulated blood so that it should reach 15 mM with respect to the anticoagulated blood at the time of monitoring thrombus formation, the blood was added to a syringe (1-ml syringe, manufactured by Terumo Corporation), followed by inflowing the blood into the same microchip as that of Example 17 at a flow rate of 40 μl/min. Subsequently, a change in pressure was measured using the same system as that of Example 17. The pressure began to rise 15 minutes after starting the pressure measurement and it rose up to about 60 kPa.

Example 21

Figure 14:
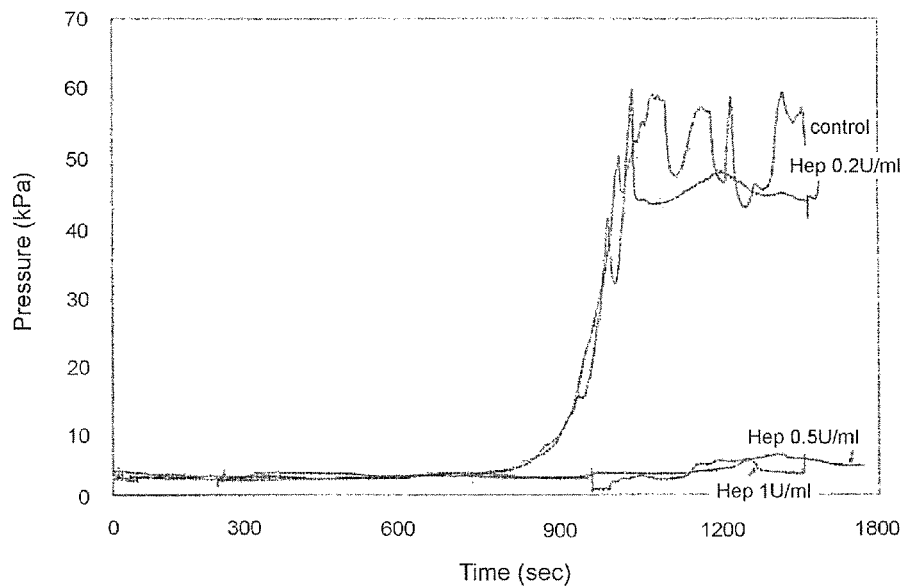
FIG. 14 is a graph showing results of pressure measurements with addition of 0 (control), 0.2, 0.5, and 1 unit/ml of heparin.

The blood sampling was carried out with the addition of an anticoagulation treatment agent in manner similar to Example 20. Subsequently, the same procedure as that of Example 20 was carried out, except that heparin was added at concentrations of 0.2 units/ml, 0.5 units/ml, and 1 unit/ml, respectively. The measurement of pressure was then performed. The results are shown in FIG. 14.

Example 22

Figure 15:
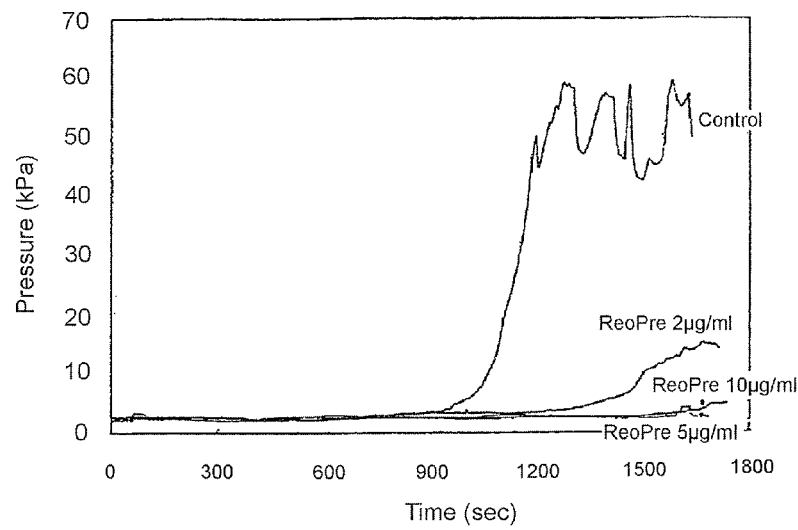
FIG. 15 is a graph showing results of pressure measurements with addition of 0 (control), 2, 5, and 10 μg/ml of heparin.

The blood sampling was carried out with the addition of an anticoagulation treatment agent in manner similar to Example 20. Subsequently, the same procedure as that of Example 20 was carried out, except that ReoPro (LILLY Co., Ltd.) was added at a concentration of 2 μg/ml. The measurement of pressure was then performed. The pressure began to rise 20 minutes after starting the pressure measurement and it rose up to about 15 kPa after 25 minutes (FIG. 15).

Example 23

A syringe-type solution-feeding system shown in FIG. 12 was used. In addition, a microchip 400, where the substrate 200 as a cover of the microchip and the substrate 100 as a body of the microchip shown in FIG. 12(B) and FIG. 12(C) were pressure-bonded with each other, was used. A discharge tube 413 made of a Teflon (registered trademark) tube was filled with mineral oil and one end thereof was connected to the microchip 400 through a connection tube 412 made of silicon rubber and the other end thereof was connected to a suction pump 414 in which a pressure sensor was installed. An inlet tube forming a channel of the microchip 400 was connected to a syringe 420 through the connection tube 412 made of silicone rubber. One end of the blood coagulation inhibitor inlet tube 422 made of Teflon (registered trademark) was connected to a liquid-feeding pump 423 and the other end thereof was connected to the terminal end of the thrombus formation chamber through the connection tube 412 made of silicone rubber. In this way, the microchip 400 was connected to the discharge tube 413, the syringe 420, and the blood coagulation inhibitor inlet tube 422, and thus an apparatus B for monitoring thrombus formation was produced. A CCD camera 430 provided with an illumination optical source 432 (LED) which was mounted on a rail 433 and movable was set under the thrombus formation chamber.

All of the grooves in the microchips had a depth of 120 μm. The channel in which the blood was introduced had a width of 800 μm and a length of 7 mm. The narrowed channel had a width of 200 μm and a length of 10 mm.

A solution was prepared such that 1 vial of PT reagent (tissue thromboplastin, Sysmex Corporation) was dissolved in 1 ml of purified water and then dialyzed in purified water, the dialyzed product in purified water was mixed with collagen type I (manufactured by Nitta Gelatin Inc.) at a ratio of 1:1. The solution was then applied to the region of the substrate 200 of the microchip facing the channel of the constriction portion on the surface to be pressure-bonded with the substrate 100 of the microchip. After that, the applied portion was vacuum dried at 4° C. and the substrate 100 and the substrate 200 were then pressure-bonded with each other, thereby providing a microchip 400 having a thrombus formation chamber 411.

The blood sampling was carried out using a vacuum blood-collecting vessel in which sodium citrate provided as an anticoagulation agent was enclosed. Immediately before introducing into the syringe 420, the blood was added with calcium chloride at a final concentration of 12.5 mM and a maize-derived trypsin inhibitor at a final concentration of 25 μg/ml.

The My Flow (manufactured by Arbiotec Co., Ltd), which is a micro-feeding pump capable of monitoring the inner pressure of a liquid-feeding pump, was connected to a discharge tube 413 as a pump 414. Thus, the suction was performed at a rate of 15 μl/min while the inner pressure of the channel was monitored.

As a blood coagulation inhibitor, 1 M of Tris-HCl (pH 10) was flown from the blood coagulation inhibitor inlet tube 422 at a flow rate of 8 μl/min. White thrombus formation was mainly observed after 4 minutes from the start of the pressure measurement, while a decrease in inner pressure was confirmed. In addition, it was confirmed that the inner pressure decreased 30 kPa after 10 minutes from the start.

Further, thrombus formation was observed by taking images while the camera 430 was moved around the thrombus-forming region in the channel. The position where the thrombus formation was observed was memorized, and the camera 430 took images while regularly moving around a plurality of specific points. As a result, growth and destruction of thrombus with time was recorded with respect to a plurality of large thrombi.

Hereinafter, reference experiments will be performed as described below to show the effectiveness of thrombin aptamers and the antisense DNAs thereof as anticoagulation treatment agents and anticoagulation releasing agents, respectively.

[Reference Experiment 1]

The blood immediately after blood sampling, the blood prepared by adding a volume of one tenth of 300 μg/ml of a maize-derived trypsin inhibitor to the first blood, and the blood prepared by adding a thrombin aptamer that recognizes exosite I to the second blood so as to be 5 μM in concentration were provided. Then, for these three kinds of the blood, the time taken for coagulation were measured in Eppendorf tubes (made of polypropylene). The sample was reversed up side down every one minute and the flowability thereof was confirmed. The blood free of additive showed a coagulation time of 9 minutes. In contrast, the blood added with the trypsin inhibitor showed a coagulation time of 22 minutes. Further, the blood added with the thrombin aptamer showed a coagulation time of 62 minutes.

Further, when 5 µM of a thrombin aptamer that recognizes exosite 1 and 5 µM of a thrombin aptamer that recognizes exosite II were used in combination, blood coagulation was not confirmed even after 3 hours even in the case of the blood free of the trypsin inhibitor. Exosite I recognition thrombin aptamer: 5'-GGTTGGTGTGGTTGG-3' SEQ ID NO. 1, Exosite II recognition thrombin aptamer: 5'-AGTCCGTGG-TAGGGCAGGTTGGGGTGACT-3' SEQ ID NO. 3.

[Reference Experiment 2]

The measurement of APTT was carried out on 200 µM of plasma with respect to each of sample A added with 10 µM of physiological saline solution, sample B added with 10 µM of 500-µM exosite I recognizing thrombin aptamer, and sample C added with 10 µl of a solution containing 500-µM exosite I recognizing thrombin aptamer and 1500-µM exosite I recognizing thrombin aptamer antisense DNA. The sample A was 44 seconds, the sample B was 2 minutes or more, and the sample C was 45 seconds.

[Reference Experiment 3]

Figure 11:
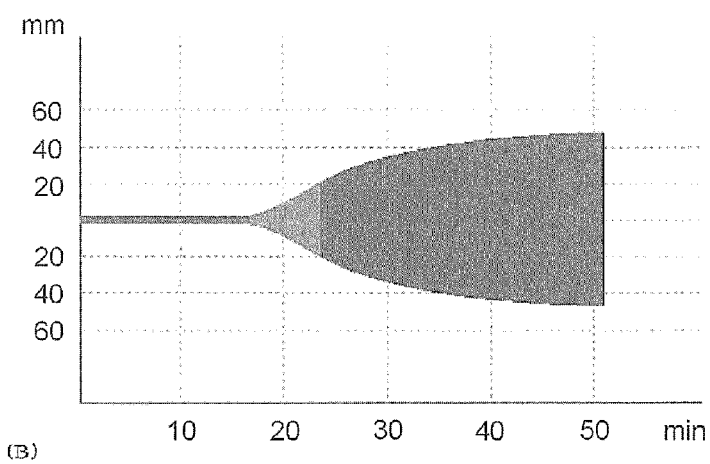
FIG. 11(A) is a result obtained by analyzing a thromboelastogram waveform of coagulation by adding 10 μM of each of aptamers for exosite I and exosite II to the blood, and after storing the blood at room temperature for 15 minutes, adding 40 μM of each of antisense DNAs of both aptamer.
FIG. 11(B) illustrates the thromboelastogram waveform of the blood just after blood sampling.
Figure 11:
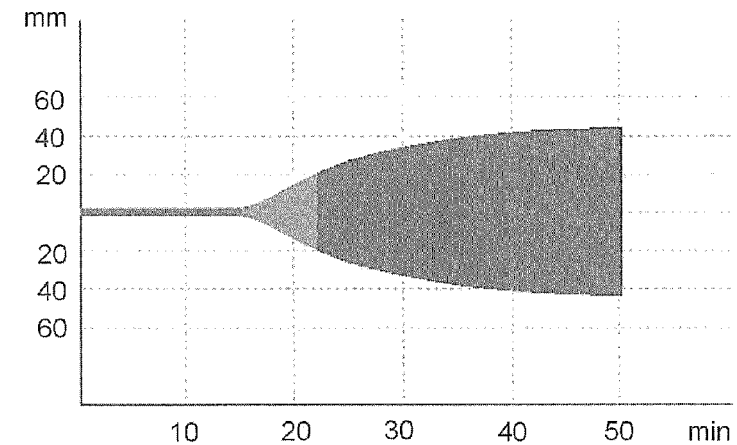

FIG. 11(A) is an analysis of a waveform of coagulation with thromboelastogram by storing the blood added with 10 µl of aptamers to exosite I and exosite II at room temperature for 15 minutes, and then by adding 40 µM of antisense DNAs of both aptamers. FIG. 11(B) is a thromboelastogram waveform of the blood just after blood sampling.

As is evident from the results of FIG. 11(A) and FIG. 11(B), it is found that the addition of two kinds of thrombin aptamers allow the blood to be stored and the antisense DNA can release the anticoagulation treatment thereof.

From the results of Reference Experiments 1 to 3, it is evident that the combination of the maize-derived trypsin inhibitor and the thrombin aptamer can effectively inhibit the coagulation of the whole blood and that the anticoagulation effect of the thrombin aptamer can be inactivated by the antisense DNA to the thrombin aptamer.

[Reference Experiment 4]

Hereinafter, the efficiencies of PMEA coating to the storage of blood and platelet adhesion on the substrate will be described.

(1) 1% PMEA-containing methanol solution prepared according to JP 04-152952 A was applied to a 2.5-ml acryl resin container (inner dimensions: 1 cm×1 cm×4.5 cm) and then dried at 90° C. for 10 minutes. Subsequently, 760 µl of the blood subjected to an anticoagulation treatment with 2% citric acid was added to each of a non-coated container and a PMEA-coated container, followed by aspirating with a pipette every 5 minutes to confirm blood coagulation.

Consequently, the non-coated container showed an apparent increase in viscosity at 30 minutes and coagulation at 60 minutes. In contrast, the PMEA-coated container showed an apparent increase in viscosity at 35 minutes, but the coagulation was prolonged to 90 minutes.

(2) The above PMEA was flatly coated on a transparent acryl plate. It was used instead of the collagen-coated plate of Example 9 (FIG. 8) and an adhesion experiment of quinacrine-labeled platelets and leucocytes in the blood was carried out in a manner similar to Example 9.

As a result, apparent adhesion or agglutination of platelets and leucocytes was observed after 10 minutes from beginning of flowing the blood. In contrast, adhesion or agglutination of platelets and leucocytes on the PMEA-coated acryl plate was not observed even after 30 minutes.

From the above results, in the apparatus for monitoring thrombus formation of the present invention, by coating the blood storage syringes, the tube, the substrate, and the like with PMEA, thrombus formation can be supressed in a place other than the thrombus monitoring chamber. Therefore, it suggested that thrombus monitoring specific to the thrombus monitoring chamber can be attained.

In the above description, the present invention has been described with reference to the preferred embodiments. However, the present invention is not limited to the examples and embodiments described above, and various modifications may be applied as long as not departing from the gist of the present invention. For example, the pressure of the pump may be set to be high and the inner diameter of the discharge tube may be set to be small. In this case, back pressure can be generated in the inlet tube and the discharge tube, so thrombus formation can be monitored while controlling the flow volume of blood under the load of inner pressure corresponding to the blood pressure. Further, the flow rate of blood at this time can be freely controlled by means of pump pressure and the degree of throttling the discharge tube.

INDUSTRIAL APPLICABILITY

The apparatus for monitoring thrombus formation and the method of monitoring thrombus formation of the present invention can be favorably used in comprehensive evaluation of blood coagulation and platelet thrombus formation under a bloodstream-equivalent environment using the whole blood or the plasma containing platelets, for evaluating the efficacy of an antithrombotic drug applied to a patient or the like.

The invention claimed is:

1. An apparatus which monitors thrombus formation by flowing anticoagulated blood through a channel that simulates a blood vessel while releasing an anticoagulation treatment or promoting blood coagulation, said apparatus comprising:
   a thrombus formation chamber in at least a part of which a thrombus inducing material that induces thrombus formation is provided;
   a first container for containing the anticoagulated blood;
   an inlet tube which is connected between the thrombus formation chamber and the first container and through which the blood is flown into the thrombus formation chamber;
   a second container containing a drug that releases the anticoagulation treatment or a drug that promotes blood coagulation; and
   a drug tube which is connected between the inlet tube and the second container and through which the drug is supplied.

2. The apparatus according to claim 1, wherein the apparatus is formed on a substrate.

3. The apparatus according to claim 1, further comprising a pump for pressurizing the inlet tube and/or the drug tube or a pump for aspirating a discharge tube which is connected to the thrombus formation chamber and provided for discharging the blood from the thrombus formation chamber.

4. The apparatus according to claim 1, further comprising a pressure-measuring apparatus.

5. The apparatus according to claim 1, wherein the thrombus inducing material comprises collagen.

6. The apparatus according to claim 5, wherein the thrombus inducing material further comprises a tissue factor.

7. The apparatus according to claim 1, further comprising a camera for taking an image of the thrombus formation chamber.

8. The apparatus according to claim 1, wherein the drug that releases the anticoagulation treatment or the drug that promotes blood coagulation is supplied, through the drug tube, to the blood flowing in the inlet tube.

* * * * *